US010842351B2

(12) United States Patent
Osaka et al.

(10) Patent No.: US 10,842,351 B2
(45) Date of Patent: Nov. 24, 2020

(54) ENDOSCOPE TREATMENT TOOL

(71) Applicant: OLYMPUS CORPORATION, Hachioji (JP)

(72) Inventors: Shingo Osaka, Tokyo (JP); Tomohiro Tsuji, Tokyo (JP); Tomohiko Mamiya, Kawasaki (JP)

(73) Assignee: OLYMPUS CORPORATION, Tokyo (JP)

( * ) Notice: Subject to any disclaimer, the term of this patent is extended or adjusted under 35 U.S.C. 154(b) by 195 days.

(21) Appl. No.: 16/216,643

(22) Filed: Dec. 11, 2018

(65) Prior Publication Data

US 2019/0104926 A1 Apr. 11, 2019

Related U.S. Application Data

(63) Continuation of application No. PCT/JP2016/070394, filed on Jul. 11, 2016.

(51) Int. Cl.
*A61B 17/122* (2006.01)
*A61B 17/128* (2006.01)
(Continued)

(52) U.S. Cl.
CPC ........ *A61B 1/00087* (2013.01); *A61B 1/0057* (2013.01); *A61B 17/1227* (2013.01);
(Continued)

(58) Field of Classification Search
CPC .......... A61B 2017/2929; A61B 17/293; A61B 17/2812; A61B 17/2816;
(Continued)

(56) References Cited

U.S. PATENT DOCUMENTS 5,464,416 A * 11/1995 Steckel ................ A61B 17/122
606/158
9,687,248 B2 * 6/2017 Satake ................. A61B 17/122
(Continued)

FOREIGN PATENT DOCUMENTS

EP 2995262 A1 3/2016
JP 2006-198388 A 8/2006
(Continued)

OTHER PUBLICATIONS

Sep. 13, 2016 International Search Report issued in International Patent Application PCT/JP2016/070394.
(Continued)

*Primary Examiner* — Wade Miles
(74) *Attorney, Agent, or Firm* — Oliff PLC

(57) ABSTRACT

An endoscope treatment tool includes: a tubular sheath part; an operation wire; an arm member; a holding tube; and a biasing member. The sheath part includes an elongated body part, and a tubular member. In a state where the holding tube and the tubular member are in contact with each other, the holding tube and the tubular member are connected to each other so as not to be rotated relative to each other about an axis and to be movable relative to each other in a direction in which a central axis of the sheath part extends. The arm member and the holding tube have a rotation restricting structure that prevents the arm member from rotating about an axis of the holding tube in a state where the arm member is in contact with the holding tube against the biasing force of the biasing member.

7 Claims, 15 Drawing Sheets

(51) Int. Cl.
   *A61B 17/00* (2006.01)
   *A61B 1/00* (2006.01)
   *A61B 1/005* (2006.01)
   *A61B 90/40* (2016.01)
   *A61B 90/00* (2016.01)
   *A61B 1/018* (2006.01)

(52) U.S. Cl.
   CPC .......... *A61B 17/1285* (2013.01); *A61B 90/40* (2016.02); *A61B 1/00133* (2013.01); *A61B 1/018* (2013.01); *A61B 2017/00477* (2013.01); *A61B 2090/037* (2016.02)

(58) Field of Classification Search
   CPC .... A61B 2017/2947; A61B 2017/2931; A61B 17/1227; A61B 17/128; A61B 17/1285
   See application file for complete search history.

(56) References Cited

U.S. PATENT DOCUMENTS

| | | | | |
|---|---|---|---|---|
| 2005/0149063 | A1* | 7/2005 | Young | A61B 17/1285 606/142 |
| 2006/0224165 | A1* | 10/2006 | Surti | A61B 17/29 606/142 |
| 2008/0140089 | A1 | 6/2008 | Kogiso et al. | |
| 2009/0326558 | A1* | 12/2009 | Cui | A61B 17/1227 606/143 |
| 2010/0152753 | A1* | 6/2010 | Menn | A61B 17/10 606/158 |
| 2013/0211432 | A1* | 8/2013 | Terada | A61B 17/122 606/151 |
| 2014/0171974 | A1* | 6/2014 | Zhu | A61B 17/122 606/144 |
| 2015/0190136 | A1* | 7/2015 | Cohen | A61B 17/1227 606/143 |
| 2017/0215886 | A1* | 8/2017 | Muyari | A61B 17/1285 |
| 2018/0333156 | A1* | 11/2018 | Hayashi | A61B 1/00112 |
| 2019/0133597 | A1* | 5/2019 | Osaka | A61B 17/1227 |
| 2019/0133598 | A1* | 5/2019 | Uesaka | A61B 17/1227 |

FOREIGN PATENT DOCUMENTS

| | | |
|---|---|---|
| JP | 2007-159794 A | 6/2007 |
| JP | 2008-132290 A | 6/2008 |
| JP | 2010-136819 A | 6/2010 |
| JP | 2012-200415 A | 10/2012 |
| JP | 2013-063109 A | 4/2013 |
| JP | 5750624 B2 | 7/2015 |
| WO | 2008/090978 A1 | 7/2008 |

OTHER PUBLICATIONS

Dec. 17, 2019 Office Action issued in Japanese Patent Application No. 2018-527050.
Oct. 8, 2019 Office Action issued in Japanese Patent Application No. 2018-527050.

* cited by examiner

US 10,842,351 B2

ENDOSCOPE TREATMENT TOOL

CROSS REFERENCE TO RELATED APPLICATIONS

This application is a continuation application based on a PCT Patent Application No. PCT/JP2016/070394, filed on Jul. 11, 2016, the entire content of which is hereby incorporated by reference.

BACKGROUND OF THE INVENTION

Field of the Invention

The present invention relates to an endoscope treatment tool.

Description of the Related Art

Various treatment tools used with an endoscope are known.

For example, Japanese Unexamined Patent Application, First Publication No. 2013-63109 discloses a clip for ligating tissue under endoscopic view. Also, Japanese Unexamined Patent Application, First Publication No. 2012-200415 discloses a mechanism capable of rotating a clip so as to align a clip to a desired orientation by hand operation.

SUMMARY

An endoscope treatment tool includes: a tubular sheath part; an operation wire arranged inside the sheath part and capable of protruding from and retracting into a distal end of the sheath part; an arm member connected to a distal end of the operation wire, having a pair of distal end portions, and capable of opening and closing, the arm member being rotatable integrally with the operation wire; a holding tube arranged at the distal end of the sheath part, a portion of the arm member being inserted in the holding tube; and a biasing member having a biasing force for moving the arm member toward a distal end side of the holding tube. The sheath part includes an elongated body part, and a tubular member fixed to a distal end of the body part and holding the holding tube coaxially with the holding tube. In a state where the holding tube and the tubular member are in contact with each other, the holding tube and the tubular member are connected to each other so as not to be rotated relative to each other about an axis and to be movable relative to each other in a direction in which a central axis of the sheath part extends. The arm member and the holding tube have a rotation restricting structure that prevents the arm member from rotating about an axis of the holding tube in a state where the arm member is in contact with the holding tube against the biasing force of the biasing member. The arm member rotates integrally with the operation wire in a state where the arm member is moved to the distal end side of the holding tube by the biasing force of the biasing member.

The rotation restricting structure may include: an engagement part provided in the holding tube and engages with the arm member when the arm member comes into contact with the holding tube against the biasing force of the biasing member; and an engaged part provided on the arm member and engaged with the engagement part.

The engagement part may be a concave portion provided on the holding tube, and the engaged part may be a projection protruding from the arm member and capable of entering the concave portion.

The engagement part may be a convex portion provided on the holding tube, and the engaged part may be a recess formed in the arm member and into which the convex portion can enter.

The biasing member may be composed of a spring disposed inside the holding tube, and the arm member may be separated from a distal end of the holding tube by the biasing force of the spring in a state where an operation force is not applied to the operation wire.

The endoscope treatment tool may further include an operation unit connected to a proximal end of the sheath part and moving the operation wire forward and backward.

The endoscope treatment tool may further include a connecting member that connects between the operation wire and the arm member, and the connecting member may be configured to release a connection between the operation wire and the arm member when the arm member is closed until the pair of distal end portions are close to each other.

DETAILED DESCRIPTION OF THE PREFERRED EMBODIMENTS

Figure 1:
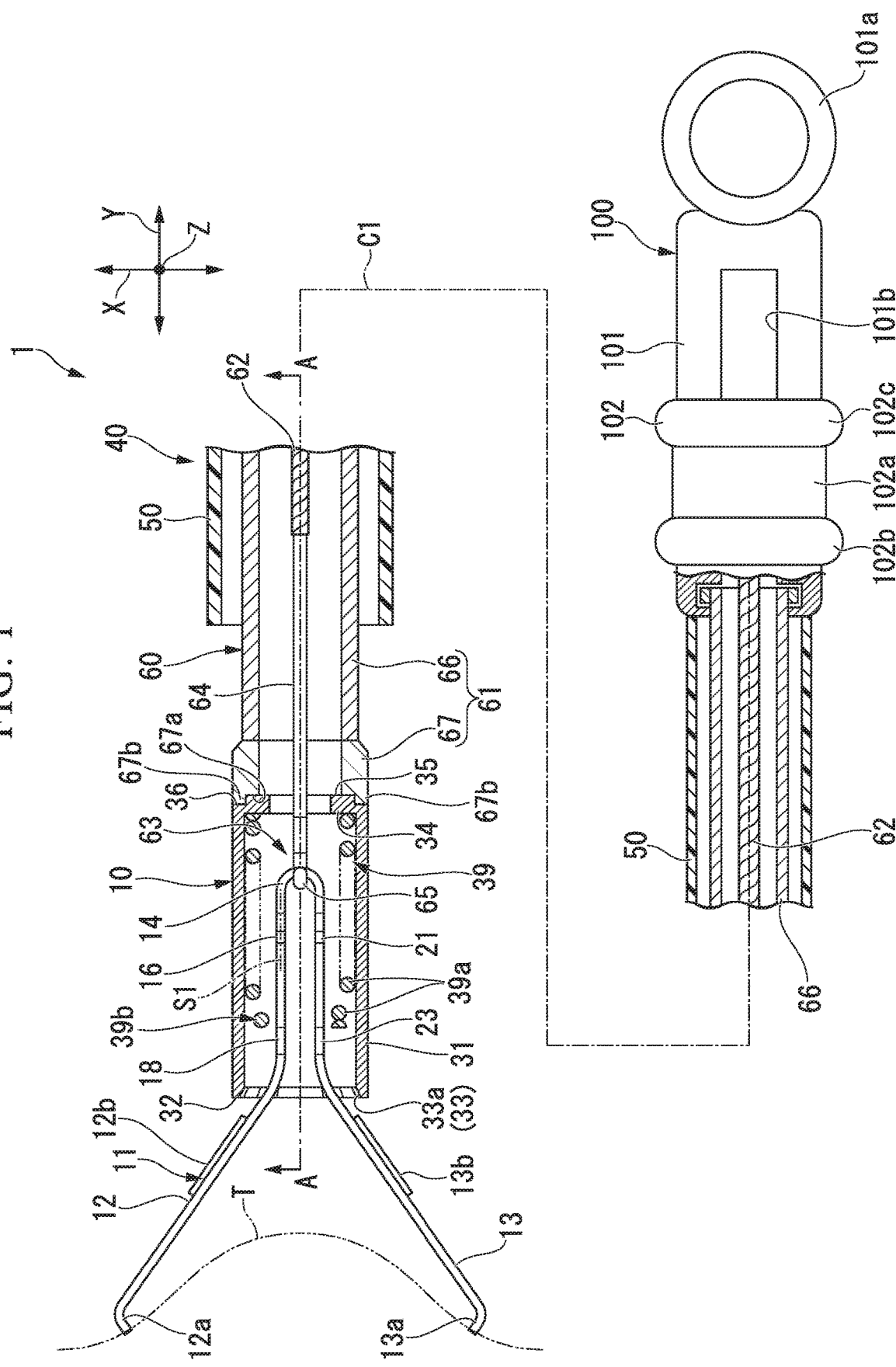
FIG. 1 is a partial cross-sectional view of an endoscope treatment tool according to an embodiment of the present invention.

An embodiment of the present invention will be described.

The endoscope treatment tool 1 of the present embodiment is an elongated treatment tool that can be inserted into a treatment instrument channel of an endoscope. The endoscope treatment tool 1 of the present embodiment is a ligating apparatus that can ligate tissue using the clip unit 10.

The endoscope treatment tool 1 includes a clip unit 10 and a treatment instrument main body 40.

The clip unit 10 includes an arm member 11, a holding tube 31, and a helical spring 39 (a biasing member). Each member constituting the clip unit 10 is preferably biocompatible. For example, the clip unit 10 is made of a material such as a cobalt chrome alloy, titanium, stainless steel or the like. The clip unit 10 may also be configured to allow observation under MRI (Nuclear Magnetic Resonance Imaging) perspective.

The arm member 11 has a first arm portion 12, a second arm portion 13, and a central portion 14.

The first arm portion 12 and the second arm portion 13 are arranged so as to extend from the proximal end side toward the distal end side and face each other. The first arm portion 12 and the second arm portion 13 are formed so as to be separated from each other in a natural state (a state in which no external force is applied by the holding tube 31 or the like) as they go from the proximal end side toward the distal end side. In the side view shown in FIG. 1, the first arm portion 12 and the second arm portion 13 are formed to be line-symmetrical with respect to the central axis C1 of the holding tube 31.

In the first arm portion 12 and the second arm portion 13, a cross-sectional shape orthogonal to the longitudinal direction on the distal end side is formed in a shape having a rounded shape so as to form an arc shape. More specifically, the vicinity of the center in the orthogonal direction Z (described later) on the outer surfaces of the first arm portion 12 and the second arm portion 13 is formed in a curved surface shape that protrudes outward. As a result, the strength of the first arm portion 12 and the second arm portion 13 against bending is improved. Further, since the first arm portion 12 and the second arm portion 13 are formed in a rounded shape as described above, the friction resistance against the mantle tube 50, which will be described later, is reduced, so that they can smoothly advance and retreat inside the mantle tube 50. Further, the first arm portion 12 and the second arm portion 13 have projections 12b, 13b that protrude toward the outside of the first arm portion 12 and the second arm portion 13 along the longitudinal direction of the first arm portion 12 and the second arm portion 13, on the outer surfaces of the first arm portion 12 and the second arm portion 13. The projections 12b, 13b constitute a rotation restricting structure for preventing the arm member 11 from rotating around the central axis C1 of the holding tube 31 described later.

Here, as shown in FIG. 1, an opposing direction X is defined as a direction where the first arm portion 12 and the second arm portion 13 are opposed, an axial direction Y is defined as parallel to the center axis C1 of the holding tube 31, and an orthogonal direction Z is defined as orthogonal to the opposing direction X and the axial direction Y respectively.

Figure 2:
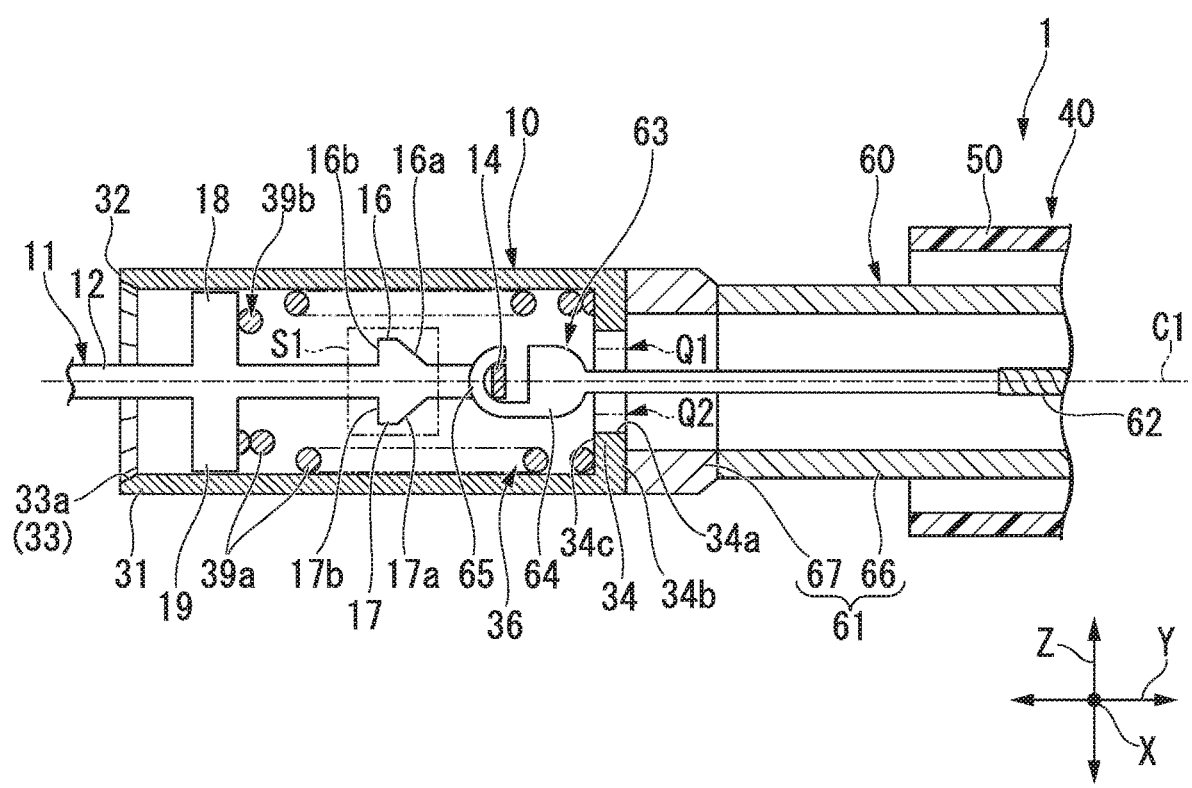
FIG. 2 is a cross-sectional view taken along the line A-A of FIG. 1.

As shown in FIG. 2, the first arm portion 12 has a claw 12a extending from the first arm portion 12 toward the second arm portion 13 at the distal end portion of the first arm portion 12. Further, the first arm portion 12 has two first latched parts 16, 17 at the proximal end portion of the first arm portion 12. The first latched parts 16, 17 are provided so as to protrude from the side surface of the first arm portion 12 in the orthogonal direction Z on the reference surface S1 parallel to the center axis C1 of the holding tube 31. The first latched parts 16 and 17 protrude in directions opposite to each other. FIG. 2 is a view as seen in a direction orthogonal to the reference surface S1. In the plan view shown in FIG. 2, the first latched part 16 and the first latched part 17 are formed to be axisymmetric with respect to the central axis C1 of the holding tube 31. As shown in FIG. 2, the proximal end surface 16a of the first latched part 16 is inclined so as to be separated from the first arm portion 12 as going to the distal end side. The distal end surface 16b of the first latched part 16 is perpendicular to the axial direction Y. The proximal end surface 17a and the distal end surface 17b of the first latched part 17 are formed so as to be line symmetrical to the proximal end surface 16a and the distal end surface 16b of the first latched part 16 with respect to the central axis C1 of the holding tube 31 respectively.

As shown in FIGS. 1 and 2, the first arm portion 12 has two protrusions 18, 19 at the portion of the first arm portion 12 more distal end side than the two first latched parts 16, 17. The protrusions 18 and 19 protrude in the orthogonal direction Z from the side surface of the first arm portion 12. The protrusion 18 and the protrusion 19 are formed to be axisymmetric with respect to the central axis C1 of the holding tube 31 in plan view. The length at which the protrusions 18 and 19 protrude from the first arm portion 12 in the orthogonal direction Z is longer than the length at which the two first latched parts 16 and 17 protrude from the first arm portion 12.

The second arm portion 13 has a claw 13a extending from the second arm portion 13 toward the first arm portion 12 side at the distal end portion of the second arm portion 13. Further, the second arm portion 13 has second latched parts 21, 22 and projections 23, 24 similar to the two first latched parts 16, 17 and the projections 18, 19 of the first arm portion 12. That is, the second latched parts 21, 22 protrude in the orthogonal direction Z which is a direction away from the first arm portion 12 from the side surface of the second arm portion 13. The projections 23, 24 are provided on the second arm portion 13 on the distal end side of the second latched parts 21, 22 so as to protrude in the orthogonal direction Z from the side surface of the second arm portion 13. The second latched parts 21, 22, the protrusions 23, 24, and the two first latched parts 16, 17, the protrusions 18, 19 are arranged in a sequence in the opposing direction X, respectively. That is, in the plan view shown in FIG. 2, the second latched parts 21, 22 overlap the two first latched parts 16, 17, and the protrusions 23, 24 overlap the protrusions 18, 19.

The central portion 14 is located between the proximal end portion of the first arm portion 12 and the proximal end portion of the second arm portion 13. The central portion 14 connects the first arm portion 12 and the second arm portion 13 so that the distal end portion of the first arm portion 12 and the distal end portion of the second arm portion 13 are separated from each other in a natural state. The central portion 14 is adapted to engage the central portion 14 with the connecting member 63 arranged at the distal end portion of the operation wire 62.

The above-mentioned arm member 11 is molded from a plate material formed of a cobalt chromium alloy or the like. For example, the arm member 11 is molded by a plate material punched into a predetermined shape in which the first arm portion 12, the second arm portion 13, the central portion 14, the two first latched parts 16, 17, the second latched parts 21, 22, and the protrusions 18, 19, 23, 24 are developed in a planar shape. That is, the punched plate material having the predetermined shape is bent at the connection position between the first arm portion 12 and the central portion 14 and the connection position between the second arm portion 13 and the central portion 14, and is integrally formed so as to have a C shape in a side view, whereby the arm member 11 is molded.

The holding tube 31 is a hard member formed in a cylindrical shape. The holding tube 31 is integrally formed of a material such as 64 titanium alloy (Ti—6 AL—4 V), cobalt chromium alloy or the like.

The holding tube 31 accommodates the proximal end portion of the arm member 11. The holding tube 31 has a distal end surface 32, an engagement part 33, a latching part 34, a proximal end surface 35, and a rotation restricting concave portion 36.

The distal end surface 32 of the holding tube 31 is an annular surface extending continuously in the circumferential direction of the holding tube 31.

The engagement part 33 is disposed at the distal end portion of the holding tube 31. The engagement part 33 is engageable with the arm member 11 (engaged part). The engagement part 33 is formed on at least one of the distal end surface 32 of the holding tube 31 and the inner circumferential surface at the distal end of the holding tube 31. The engagement part 33 has a rough surface in which the frictional force with respect to the arm member 11 is increased, irregularities in which the arm member 11 is engaged, and the like, thereby constituting a rotation restricting structure that prevent the arm member 11 from rotating around the central axis C1 of the holding tube 31. For example, the engagement part 33 has a concavo-convex portion 33a formed on the inner peripheral surface of the distal end portion of the holding tube 31, the concave-convex portion 33a being formed by repeating concavities and convexities at predetermined intervals around the central axis C1 of the holding tube 31. The concave portion of the concavo-convex portion 33a is a recess of a size that allows the projection 12b formed in the first arm portion 12 of the arm member 11 or the projection 13b formed in the second arm portion 13 to enter. The concave portion of the concavo-convex portion 33a is provided, for example, at 45° around the central axis C1 of the holding tube 31. The engagement part 33 may have a tapered shape formed to extend over the entire circumference of the holding tube 31 and expand in diameter toward the distal end side of the holding tube 31 at the distal side of the holding tube 31.

The latching part 34 is arranged on the inner peripheral surface of the holding tube 31. The latching part 34 is formed over the entire circumference of the holding tube 31. The latching part 34 protrudes from the inner peripheral surface of the holding tube 31 toward the central axis C1 of the holding tube 31. When viewed in the axial direction Y shown in FIG. 7, an edge portion 34a of the latching part 34 on the side of the center axis C1 of the retaining tube 31 is formed in a circular shape coaxial with the retaining tube 31. The proximal end surface 34b (end surface of the proximal end side) and the distal end surface 34c (end surface of the distal end side) of the latching part 34 are orthogonal to the axial direction Y. In the present embodiment, the portion of the first arm portion 12 more proximal end side than the projections 18, 19, the portion of the second arm portion 13 more proximal end side of the projections 23, 24, and the central portion 14 can be inserted into the latching part 34.

The inner diameter of the latching part 34 is larger than the length L1 from the end of the first latched part 16 to the end of the first latched part 17 in the orthogonal direction Z. In addition, in an initial state to be described later, a part of each of the two first latched parts 16, 17 is set so as to overlap with the latching part 34 when viewed from the axial direction Y.

The proximal end surface 35 of the holding tube 31 is a flat surface which can be brought into contact (or in close proximity with a slight gap) to a distal end surface of a distal end member 67 described later.

The rotation restricting concave portion 36 is a concave portion continuous with the proximal end surface 35 of the holding tube 31 and formed as recess from the proximal end surface 35 of the holding tube 31 toward the distal end side. The rotation restricting concave portion 36 is formed at at least one portion of the proximal end portion of the holding tube 31. In the present embodiment, the rotation restricting concave portion 36 is formed in two places facing each other across the center axis C1 of the holding tube 31 in the radial direction of the holding tube 31.

Figure 3:
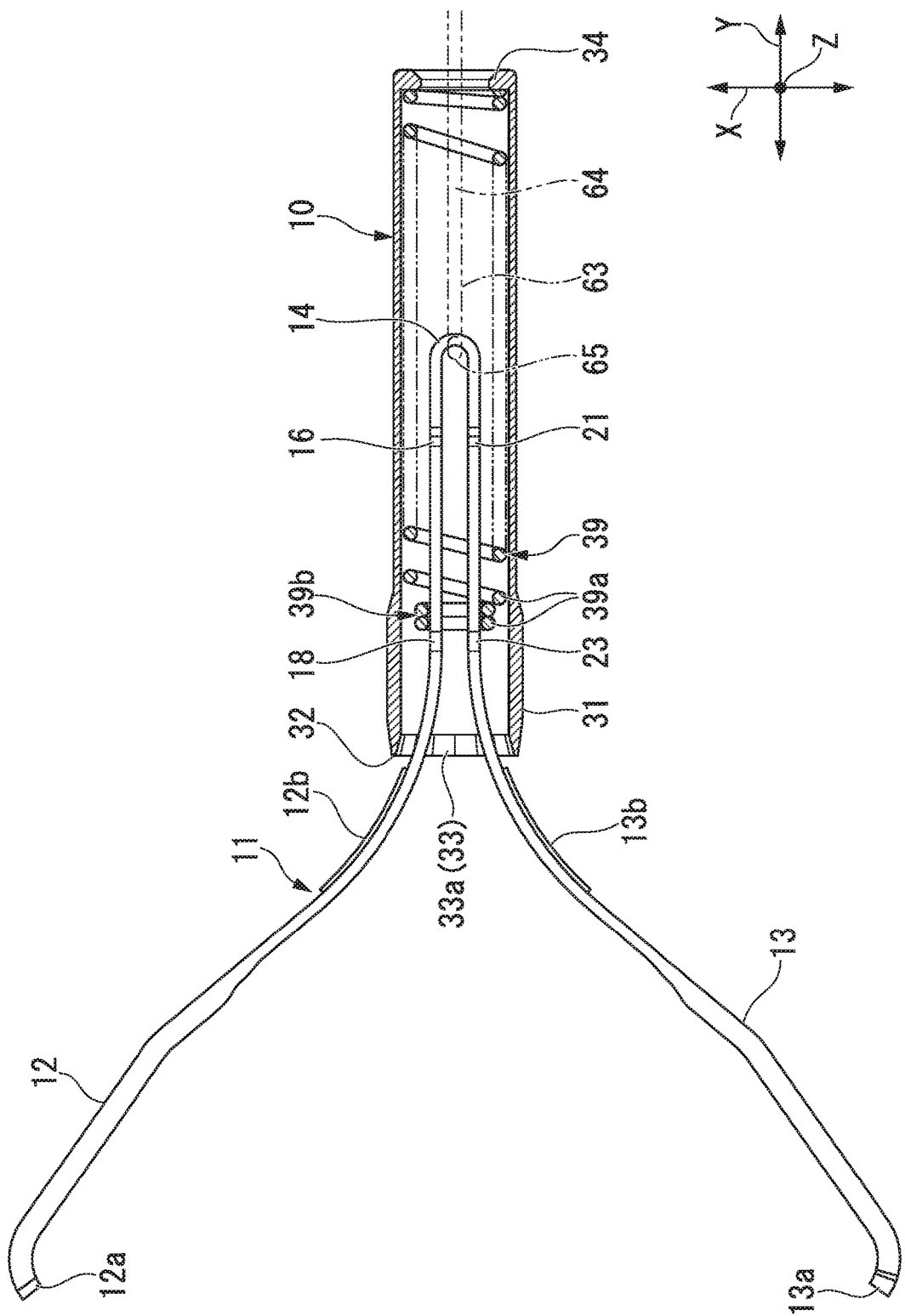
FIG. 3 is a partial cross-sectional view of a clip unit of the endoscope treatment tool.

The helical spring 39 is a biasing member accommodated in the holding tube 31. As shown in FIG. 3, the distal end portion of the helical spring 39 can contact the projections 18, 19, 23, 24 of the arm member 11. The proximal end portion of the helical spring 39 is engaged with the latching part 34. The proximal end portion of the helical spring 39 and the latching part 34 may be fixed by welding or the like and may not be fixed. In the present embodiment, a portion of the first arm portion 12 more proximal end side of the protruding portions 18, 19, a portion of in the second arm portion 13 more proximal end side of the protruding portions 23, 24, and the central portion 14 can be inserted into the coil spring 39. When the protrusions 18, 19, 23, 24 move to the proximal end side against the biasing force of the helical spring 39, the protrusions 18, 19, 23, 24 are latched at the distal end of the helical spring 39. In addition, the helical spring 39 may have the seat winding portion 36b at the distal end portion of the helical spring 39 configured so that the inner diameter is smaller at the distal end than at other portions.

In the initial state of the clip unit 10 shown in FIGS. 1 and 2, the proximal end portion of the first arm portion 12, the proximal end portion of the second arm portion 13, and the central portion 14 are accommodated at portions more distal end side than the latching part 34. The two first latched parts 16, 17 and the second latched parts 21, 22 are not in contact with the latching part 34 of the holding tube 31. The element wires 39a of the helical spring 39 adjacent to each other in the axial direction Y are separated from each other. The distal end portions of the first arm portion 12 and the second arm portion 13 (a pair of distal end portions) are in an open state relatively separated from each other in the initial state of the clip unit 10.

The treatment instrument main body 40 is a device for ligating the tissue by the clip unit 10 in response to an operation by an operator.

The treatment instrument main body 40 has a mantle tube 50, an insertion portion 60, and an operation unit 100.

The mantle tube 50 is a tubular member having flexibility. As the material of the mantle tube 50, for example, a fluororesin such as PTFE (polytetrafluoroethylene) or a resin material such as HDPE (high density polyethylene) can be used.

The insertion portion 60 is inserted into the mantle tube 50 so as to be able to move back and forth inside the mantle tube 50. The insertion portion 60 includes a sheath part 61, an operation wire 62, and a connecting member 63.

The sheath part 61 has a coil sheath (main body part of the sheath part) 66 and a distal end member (tubular member) 67. The coil sheath 66 is formed of stainless steel such as SUS 301 having high compression resistance strength.

As the material of the coil sheath 66, it is possible to use a coil having a shape in which a strand (not shown) is densely wound in the axial direction Y. The coil sheath 66 has flexibility and is resistant to compressive force in the axial direction Y. The inner diameter of the coil sheath 66 is substantially equal to the inner diameter of the helical spring 39.

The distal end member 67 is fixed to the distal end portion of the coil sheath 66.

The distal end member 67 is formed in a cylindrical shape with stainless steel or the like. The inner diameter of the distal end member 67 is substantially equal to the inner diameter of the coil sheath 66. The outer diameter of the distal end member 67 is substantially equal to the outer diameter of the coil sheath 66.

The distal end portion of the distal end member 67 has a planar distal end surface 67a oriented toward the distal end side and a rotation restricting convex portion 67b further projecting to the distal end side from the distal end surface.

The distal end surface 67a of the distal end member 67 may be capable of contacting the proximal end surface 35 of the holding tube 31.

The rotation restricting convex portion 67b is a convex portion that can be inserted into the rotation restricting concave portion 36 of the holding tube 31. The rotation restricting protrusion 67b is formed at the distal end portion of the distal end member 67 by at least one, at most the number equal to or less than the number of the rotation restricting concave portions 36, corresponding to the number of the rotation restricting concave portions 36 of the holding tube 31. In a state where the holding tube 31 is appropriately mounted on the distal end member 67, the rotation restricting convex portion 67b of the distal end member 67 is inserted into the rotation restricting concave portion 36 of the holding tube 31, and the distal end surface of the distal end member 67 is in contact with (or is in close proximity with a small gap to) the proximal end surface 35 of the holding tube 31.

The operation wire 62 is inserted into the sheath part 61 so as to be able to advance and retreat within the sheath part 61. The operation wire 62 is formed of a metal single wire or a stranded wire.

The connecting member 63 is fixed to the operation wire 62.

The connecting member 63 has a main body part 64 fixed to the operation wire 62 and a hook portion 65 which is engageable with the central portion 14 of the arm member 11 and has flexibility.

The hook portion 65 can be deformed linearly by a force exceeding a predetermined force amount. The hook portion 65 may be an elastically deformable member or a plastically deformable member. Further, the hook portion 65 may be broken by a force exceeding a predetermined force amount. Before the ligation procedure, the hook portion 65 is J-shaped, and holds the arm member 11 so that the central portion 14 of the arm member 11 does not separate from the connecting member 63. The hook portion 65 is linearly deformed by the force that the slider 102 described later moves to the proximal end side of the operation unit main body 101 by the operator. The amount of force required for the hook portion 65 to start deformation is set so as to correspond to the configuration of the clip unit 10, such that the hook portion 65 begins to deform after the arm member 11 is appropriately drawn into the holding tube 31 (after being brought into a latched state described later).

The operation unit 100 is attached to the proximal end portion of the insertion portion 60.

As shown in FIG. 1, the operation unit 100 includes an operation unit main body 101 and a slider 102.

The operation unit main body 101 is attached to the proximal end portion of the coil sheath 66. The operation unit main body 101 and the coil sheath 66 are connected so as to be relatively rotatable. The operation unit main body 101 is formed in a bar shape extending in the axial direction Y. The operation unit main body 101 has a finger hooking part 101a at the proximal end portion thereof. The operation unit main body 101 has a flat part 101c on the proximal end side of the finger hooking part 101a (see FIG. 4) so that the operation unit 100 can be gripped easily with both hands. The operation unit main body 101 has a slit 101b extending in the axial direction Y.

The slider 102 is externally fitted to the operation unit main body 101 and provided so as to be slidable in the axial direction Y with respect to the operation unit main body 101. The slider 102 is fixed to the proximal end of the operation wire 62. The slider 102 is formed in a cylindrical shape. The slider 102 has a concave portion 102a extending over the entire circumference of the outer peripheral surface of the slider 102. Further, the slider 102 has a pair of flanges 102b and 102c. The pair of flanges 102b and 102c are formed so that the concave portion 102a is positioned between the pair of flanges 102b and 102c in the axial direction Y.

Figure 4:
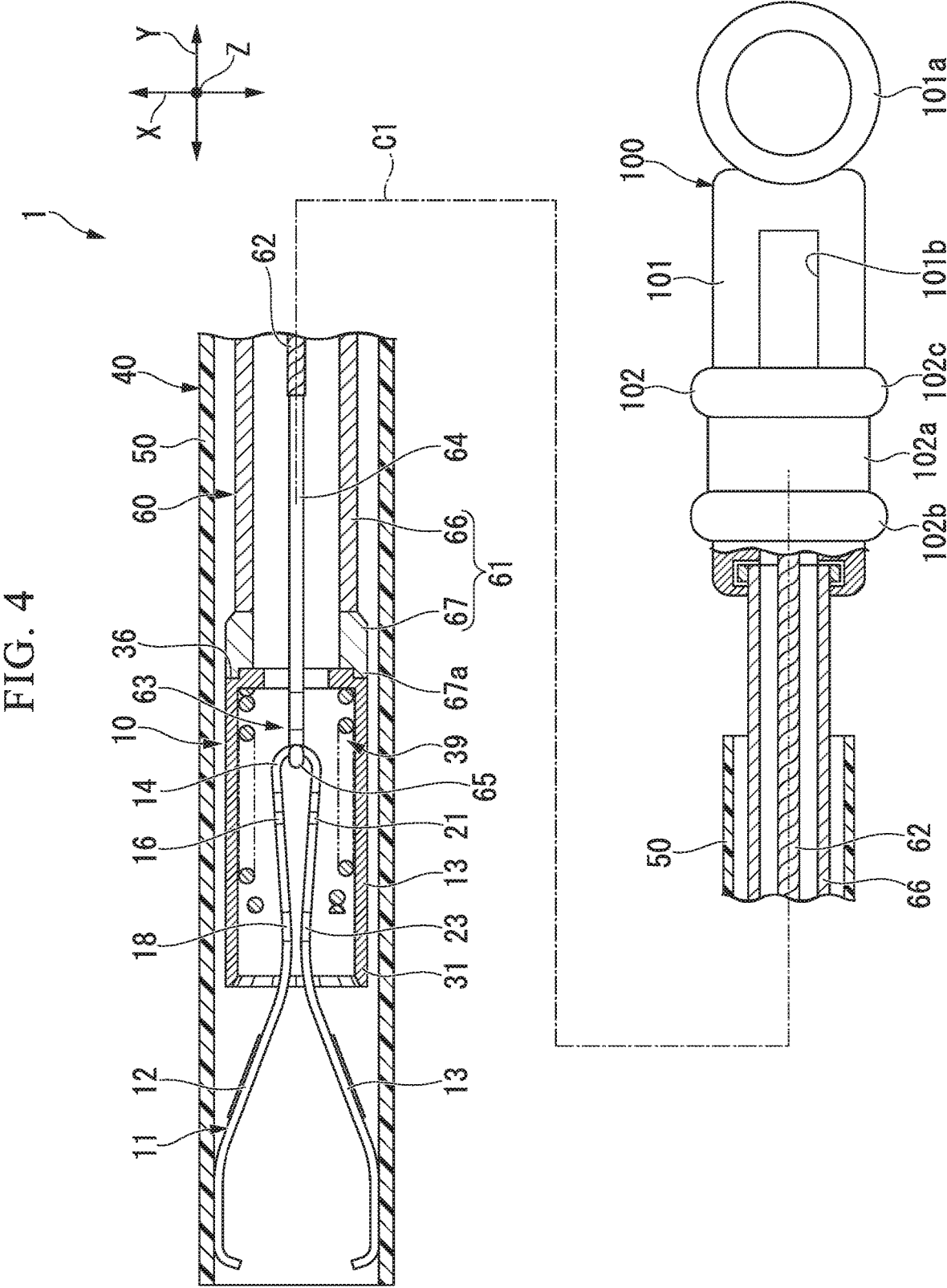
FIG. 4 is a partial cross-sectional view for explaining an operation of the endoscope treatment tool.
Figure 8:
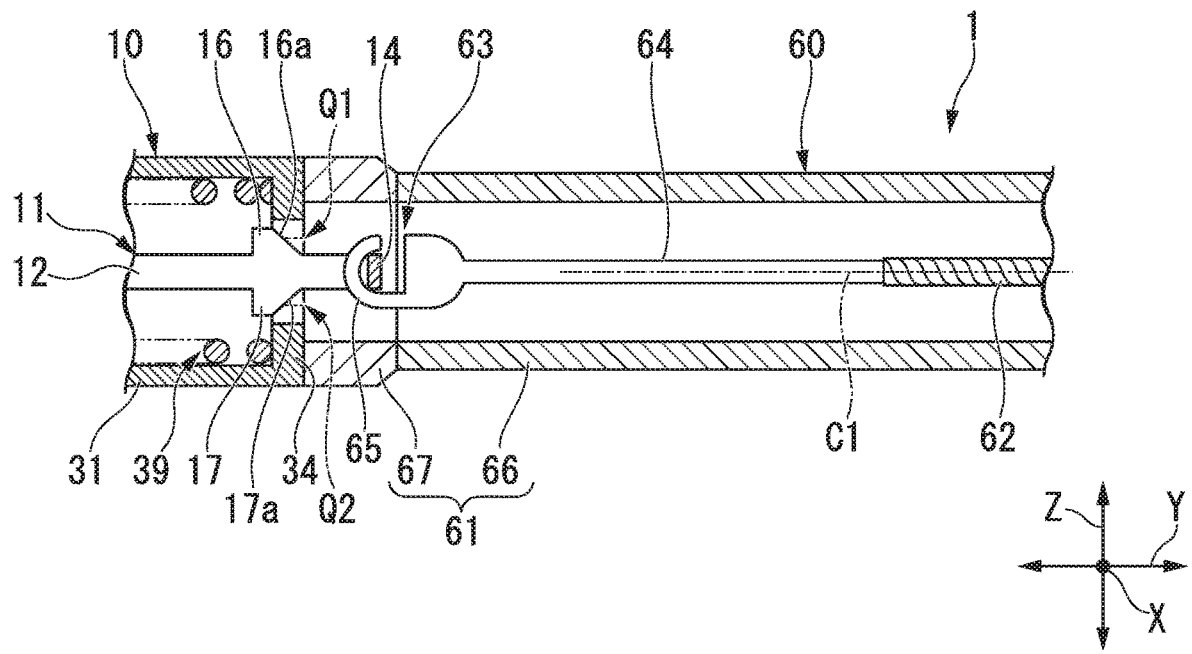
FIG. 8 is a partial cross-sectional view for explaining the operation of the endoscope treatment tool.

The pair of flanges 102b and 102c may have an elliptical shape when viewed in the axial direction Y (see FIGS. 4 and 8). As a result, the slider 102 becomes easy to grip, and it is possible to save space when packing the operation unit 100 of the endoscope treatment tool 1.

Figure 5:
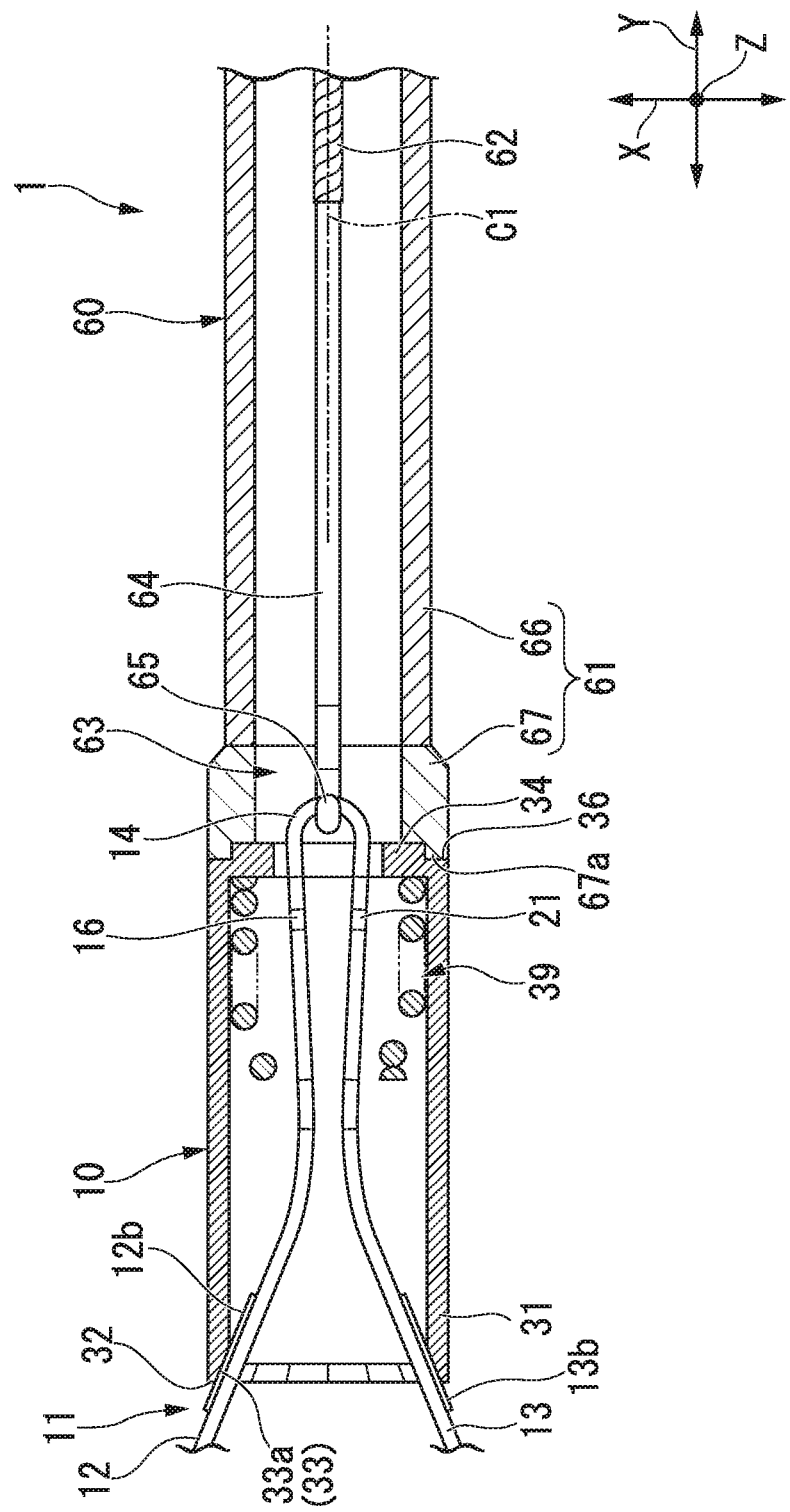
FIG. 5 is a partial cross-sectional view for explaining the operation of the endoscope treatment tool.
Figure 6:
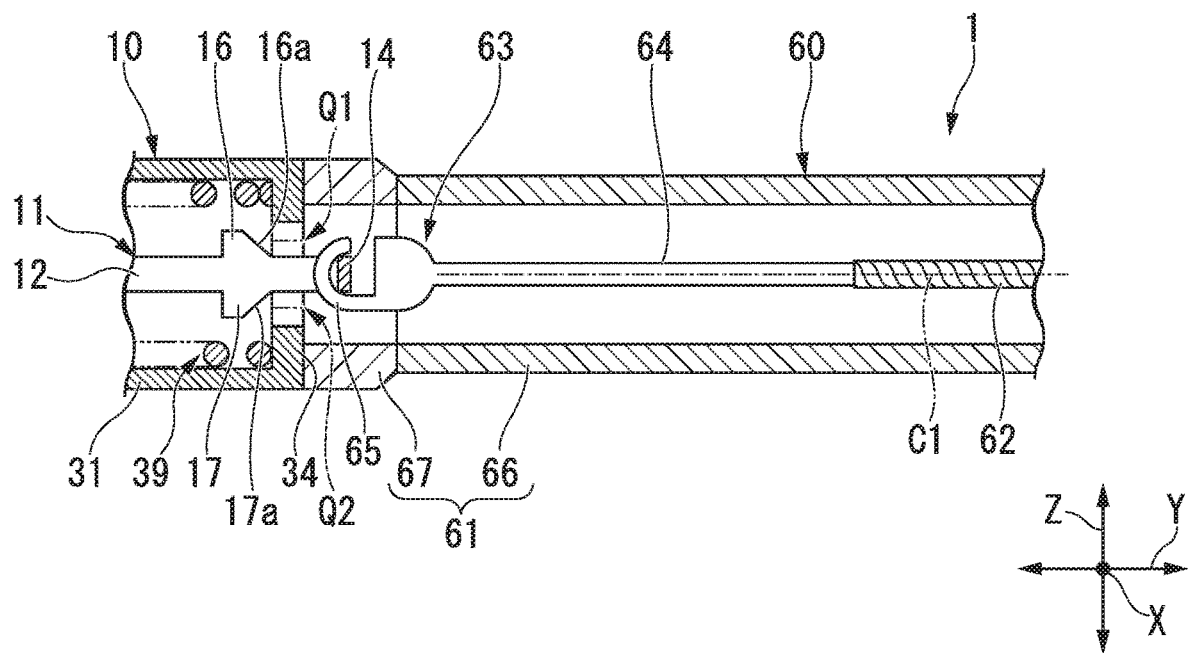
FIG. 6 is a partial cross-sectional view for explaining the operation of the endoscope treatment tool.

As shown in FIG. 5, the slider 102 has a groove 102e extending in the orthogonal direction Z in the cylindrical hole 102d of the slider 102. The movement range of the slider 102 in the axial direction Y with respect to the operation unit main body 101 is restricted by engaging the slider 102 with the slit 101b of the operation unit main body 101.

When the operation unit main body 101 is rotated about the longitudinal axis of the operation unit main body 101, the slider 102 rotates integrally with the operation unit main body 101. When the slider 102 rotates integrally with the operation unit main body 101, the slider 102 rotates the operation wire 62. At this time, since the operation unit main body 101 and the coil sheath 66 are relatively rotatable, when the operation unit main body 101 is rotated about the longitudinal axis of the operation unit main body 101, the operation wire 62 rotates with respect to the coil sheath 66. When the operation wire 62 rotates with respect to the coil sheath 66, the arm member 11 rotates with respect to the sheath part 61 and the holding tube 31 at the distal end portion of the sheath part 61. That is, when the operation unit main body 101 is rotated about the longitudinal axis of the operation unit main body 101, the arm member 11 can be rotated with respect to the sheath part 61 and the holding tube 31 at the distal end portion of the sheath part 61.

The operation of the endoscope treatment tool 1 of the present embodiment will be described.

Figure 7:
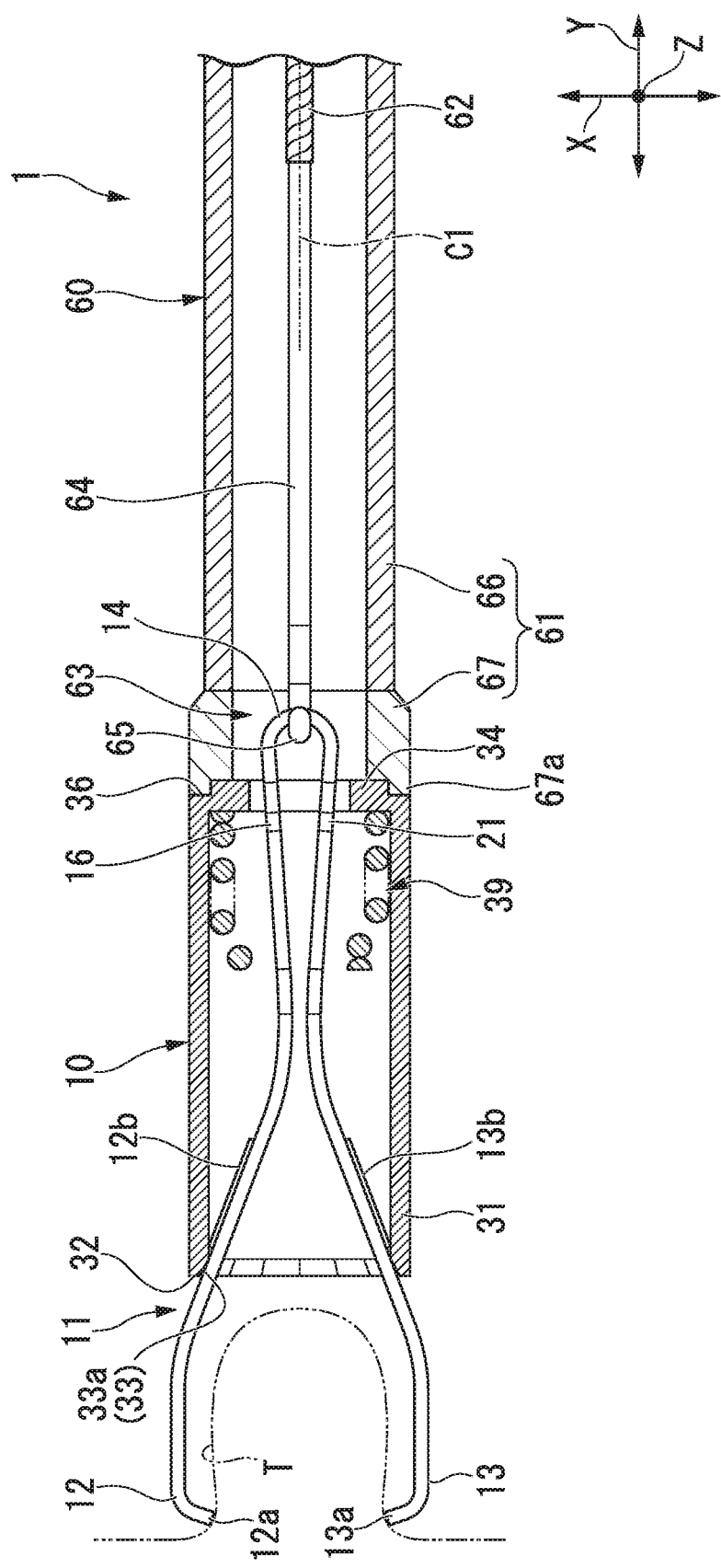
FIG. 7 is a partial cross-sectional view for explaining the operation of the endoscope treatment tool.

In the clip unit 10 configured as described above, the first arm portion 12 and the second arm portion 13 are separated from each other in the opposing direction X in the initial state. Therefore, as shown in FIG. 7, when the first latched part 16 is projected to the proximal end side, the first latched part 16 overlaps the portion at the position P1 at the edge portion 34a of the latching part 34. That is, when the first arm portion 12 is moved toward the proximal end side with respect to the holding tube 31 while maintaining the position in the opposing direction X and the orthogonal direction Z of the first arm portion 12 with respect to the holding tube 31 in the initial state, the first latched part 16 comes into contact with the edge portion 34a at the position P1. The position P1 of the edge portion 34a and the first latched part 16 are brought into point contact. Similarly, when the first arm portion 12 is moved to the proximal end side with respect to the holding tube 31, the first latched part 17 comes into contact with the edge portion 34a at the position P2. The position P2 of the edge portion 34a and the first latched part 17 are brought into point contact.

A force for moving the first arm portion 12 and the second arm portion 13 toward the proximal end side with respect to the holding tube 31 is transmitted from the operation wire 62 to the central portion 14 via the connecting member 63. The hook portion 65 of the connecting member 63 maintains a J-shape in the process of moving the first arm portion 12 and the second arm portion 13 toward the proximal end side with respect to the holding tube 31. Therefore, the connecting member 63 can maintain the state in which the operation wire 62 and the arm member 11 are coupled so that the operation wire 62 and the arm member 11 are not separated.

Further, when the arm member 11 is moved to the proximal end side with respect to the holding tube 31, the first arm portion 12 and the second arm portion 13 of the arm member 11 in the opened state come into contact with the engagement part 33 arranged at the distal end portion of the holding tube 31. At this time, the projections 12b and 13b formed on the first arm portion 12 and the second arm portion 13 enter the concave portion of the concave-convex portion 33a of the engagement part 33. Thereby, the holding tube 31 and the arm member 11 are engaged with each other at the engagement part 33. As a result, the rotational movement of the arm member 11 around the central axis C1 of the holding tube 31 is restricted.

The phenomenon that the arm member 11 moves toward the proximal end side with respect to the holding tube 31 is caused by either a case where the operator pulls the arm member 11 toward the proximal side using the operation wire 62 or a case where the arm member 11 abuts against the target tissue T to be ligated and receives an external force. In this embodiment, in either case, if the arm member 11 comes into contact with the engagement part 33 of the holding tube 31, the rotational motion of the arm member 11 is restricted.

In addition, when the operation by the operator of pulling the arm member 11 toward the proximal side with the operation wire 62 is canceled or the external force received by the arm member 11 from the target tissue T disappears, the helical spring 39 (biasing member) moves the arm member 11 toward the distal end side of the holding tube 31, thereby the restriction on the rotational motion of the arm member 11 is canceled.

Next, the operation of the endoscope treatment tool 1 will be described together with the procedure of ligating the target tissue T using the clip unit 10.

Figure 11:
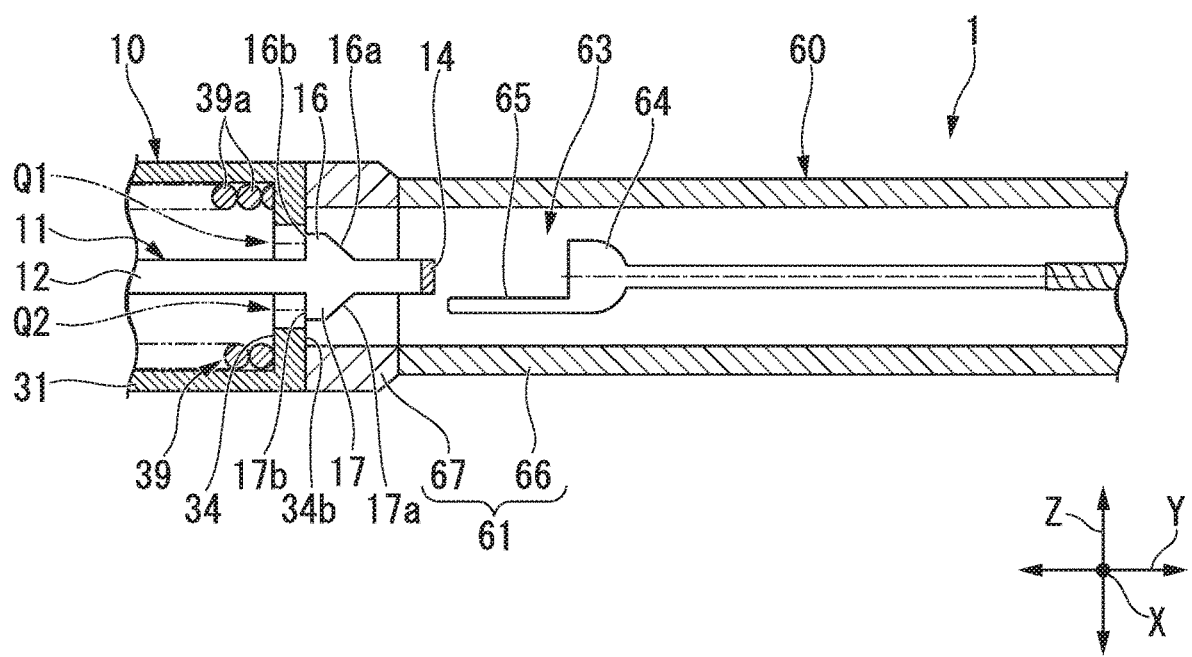
FIG. 11 is a partial cross-sectional view for explaining the operation of the endoscope treatment tool.

When the endoscope treatment tool 1 is provided to the operator of the endoscope treatment instrument 1, the clip unit 10 is attached to the distal end of the treatment instrument main body 40. Since the hook portion 65 of the treatment instrument main body 40 is positioned within the holding tube 31 of the clip unit 10, the engagement between the hook portion 65 and the central portion 14 is maintained, so that the clip unit 10 does not drop off from the treatment instrument main body 40. Further, at this time, as shown in FIG. 11, the mantle tube 50 is pushed into the insertion portion 60 so as to cover the clip unit 10 attached to the treatment instrument main body 40.

When using the endoscope treatment tool 1, an endoscope insertion portion of an endoscope (not shown) is inserted into the body of the patient. The mantle tube 50 of the endoscope treatment instrument 1 is inserted from the proximal end portion of the channel of the endoscope, and the mantle tube 50 is caused to project from the distal end portion of the channel of the endoscope. By pulling back the mantle tube 50 with respect to the insertion portion 60, the clip unit 10 protrudes from the distal end side of the mantle tube 50 as shown in FIG. 1. As a result, the first arm portion 12 and the second arm portion 13 of the clip unit 10 are in the open state shown in FIG. 1.

Next, while observing the inside of the body using the endoscope, the clip unit 10 is made to face the target tissue T in the body, by performing bending operation of the bending portion provided in the endoscope insertion portion, or the like. By pushing the endoscope treatment tool 1 into the endoscope, the first arm portion 12 and the second arm portion 13 are pressed against the target tissue T.

In addition, by rotating the operation wire 62 with respect to the sheath part 61 in the initial state, the orientation of the clip unit 10 can be adjusted. At that time, the arm member 11 rotates around the center axis C1 of the holding tube 31 with respect to the holding tube 31.

When the first arm portion 12 or the second arm portion 13 comes into contact with the target tissue T, the arm member 11 receives a pressing force from the target tissue T. That is, the arm member 11 receives an external force from the target tissue T such that the arm member 11 approaches the holding tube 31. Then, the arm member 11 moves relative to the holding tube 31 so that the distal end portion of the holding tube 31 and the arm member 11 are in contact with each other. Since the engagement part 33 is disposed at the distal end portion of the holding tube 31, the arm member 11 is engaged with the engagement part 33 in a state where the distal end portion of the holding tube 31 and the arm member 11 are in contact with each other. When the engagement part 33 arranged at the distal end portion of the holding tube 31 and the arm member 11 are engaged with each other, the rotation of the arm member 11 in the circumferential direction of the holding tube 31 is restricted. The arm member 11 is maintained so as not to rotate around the central axis C1 of the holding tube 31 as long as the engagement part 33 arranged on the holding tube 31 and the arm member 11 are in contact with each other.

When the force for pressing the arm member 11 to the target tissue T is increased, the force to rotate the arm member 11 about the central axis C1 of the holding tube 31 also increases. But since the arm member 11 and the holding tube 31 are engaged at the engagement part 33, the arm member 11 does not rotate around the center axis C1 of the holding tube 31. Further, since the engaging force between the arm member 11 and the holding tube 31 also increases in accordance with an increase in the force of pressing the arm member 11 against the target tissue T, the rotational movement of the arm member 11 is restricted in order to prevent the arm member 11 from rotating around the center axis C1 of the holding tube 31.

Therefore, the rotational position of the arm member 11 is maintained in the process of disposing the claw 12a of the first arm portion 12 and the claw 13a of the second arm portion 13 on the target tissue T.

When changing the position of the arm member 11 with respect to the target tissue T and grasping the target tissue T again, the operator separates the arm member 11 from the target tissue T. For example, by retracting the entire operation unit 100 back to the proximal side, the arm member 11 is separated from the target tissue T. At this time, since the force for pressing the arm member 11 against the target tissue T has been eliminated, the helical spring 39 moves the arm member 11 toward the distal end of the holding tube 31. As a result, the biasing force of the helical spring 39 separates the arm member 11 from the engagement part 33 of the distal end portion of the holding tube 31. In a state where the arm member 11 is separated from the engagement part 33 of the holding tube 31, there is nothing that restricts the movement of the arm member 11 around the central axis C1 of the holding tube 31 as in the initial state, thereby the arm member 11 rotates around the central axis C1 of the holding tube 31 in accordance with the operation by the operator.

When the arm member 11 is disposed at an appropriate position with respect to the target tissue T, the operator starts grasping the target tissue T using the clip unit 10. The operator pulls back the slider 102 toward the proximal side with respect to the operation unit main body 101 while maintaining the state in which the first arm portion 12 and the second arm portion 13 of the arm member 11 are in contact with the target tissue T. Alternatively, the operator pushes the operation unit main body 101 toward the distal end side with respect to the slider 102 while maintaining the state in which the first arm portion 12 and the second arm portion 13 of the arm member 11 are in contact with the target tissue T.

As the slider 102 moves toward the proximal end side of the operation unit main body 101, the state of the clip unit 10 sequentially changes from the initial state to the contact state, the transit state, and the latched state.

(Change from Initial State to Contact State)

When the operator grips the operation unit 100 and pulls back the slider 102, the first arm portion 12 and the second arm portion 13 are urged against the inner peripheral surface of the distal end portion of the holding tube 31. As a result, the first arm portion 12 elastically deforms so as to move toward the second arm portion 13, the second arm portion 13 elastically deforms so as to move toward the first arm portion 12, and the distal end portion of the first arm portion 12 and the distal end portion of the second arm portion 13 come close to each other (the first arm portion 12 and the second arm portion 13 are closed). The helical spring 39 is compressed in the axial direction Y. In this process, the first arm portion 12 and the second arm portion 13 may be separated from the engagement part 33 in some cases, but the first arm portion 12 and the second arm portion 13 are biased to the inner peripheral surface of the distal end portion of the holding tube 31. Therefore, the rotational position of the arm member 11 with respect to the holding tube 31 does not change, and the arm member 11 moves in the proximal direction of the holding tube 31.

Figure 13:
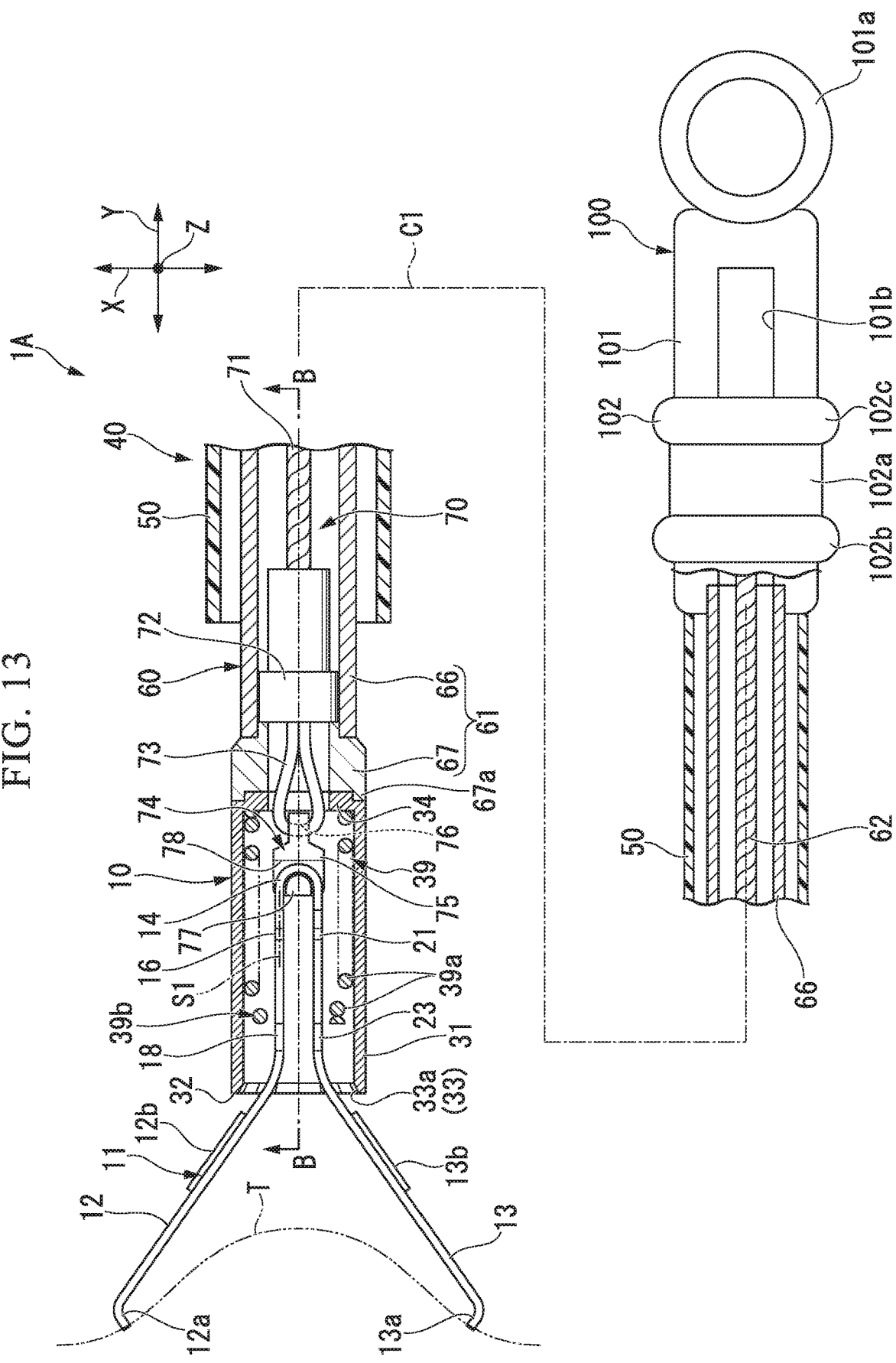
FIG. 13 is a partial cross-sectional view showing a configuration of a modified example of the endoscope treatment tool.
Figure 14:
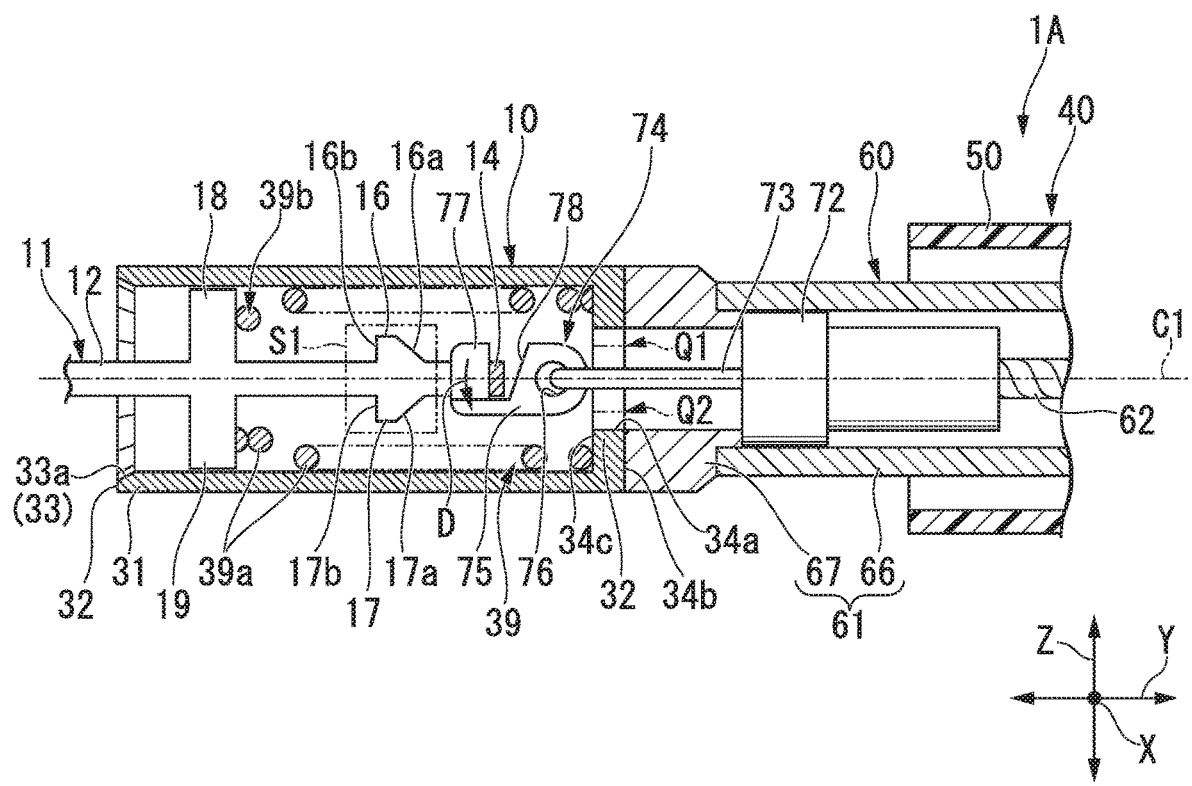
FIG. 14 is a cross-sectional view taken along the line B-B in FIG. 13.

When the slider 102 is further pulled back to the proximal end side of the operation unit main body 101, as shown in FIGS. 7, 13 and 14, the two first latched parts 16, 17 and the second latched parts 21, 22 come into contact with the latching part 34 of the holding tube 31. At this time, as shown in FIG. 7, the first latched part 16 comes into contact with the position P1 and the first latched part 17 comes into contact with the position P2 at the edge portion 34a of the holding tube 31.

When the clip unit 10 is in the above-mentioned contact state, the arm member 11 is in a closed state. When the clip unit 10 is in the above-mentioned contact state, the shape of the hook portion 65 is maintained in a J-shape. Therefore, the engagement state between the hook portion 65 and the central portion 14 is maintained.

(Change from Contact State to Transit State)

Figure 9:
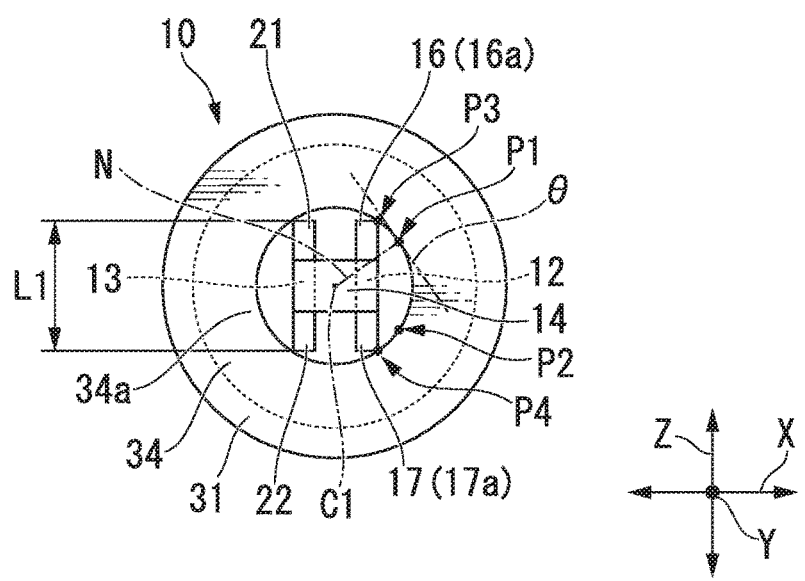
FIG. 9 is a rear view of the clip unit.

The proximal end surfaces 16a and 17a of the two first latched parts 16 and 17 are inclined as described above, and the edge portion 34a has a circular shape. Therefore, when the slider 102 is pulled back further, the first latched part 16 receives a vertical forcee from the edge portion 34a in parallel to the normal line N orthogonal to the tangent line θ of the edge portion 34a at the position P1 where the first latched part 16 is brought into contact with the edge portion 34a of the latching part 34 when viewed in the axial direction Y shown in FIG. 9. Due to this vertical force, the first latched part 16 of the first arm portion 12 moves in the opposite direction X so as to approach the second arm portion 13.

Figure 10:
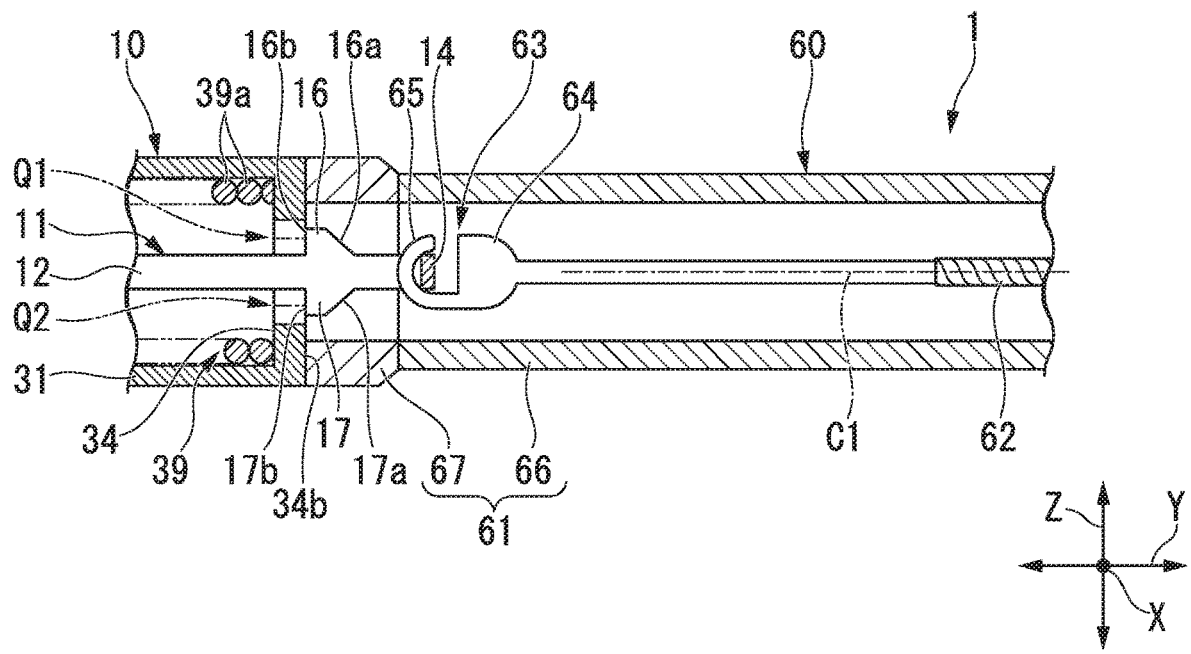
FIG. 10 is a partial cross-sectional view for explaining the operation of the endoscope treatment tool.
Figure 12:
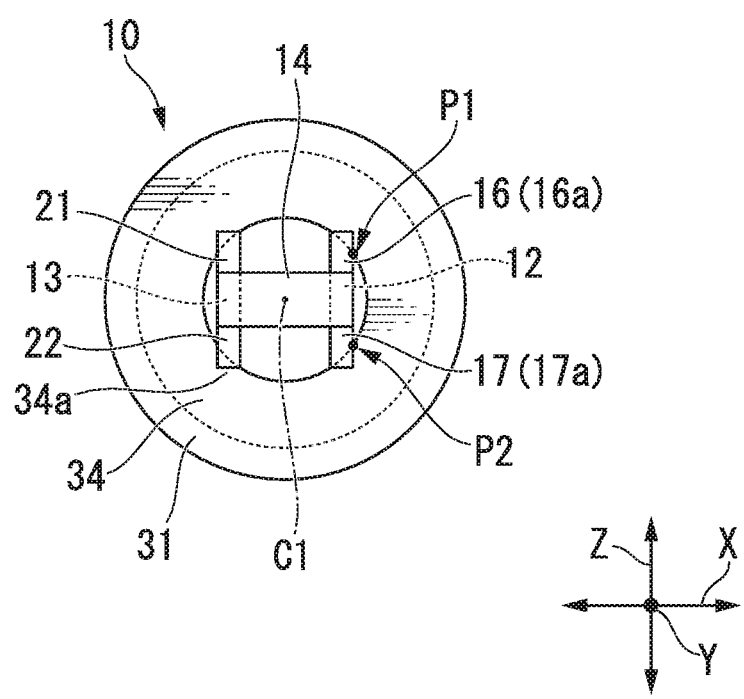
FIG. 12 is a rear view of the clip unit.

When the slider 102 is further continued to be pulled back to the proximal end side of the operation unit main body 101, as shown in FIGS. 8 to 12, while the two first latched parts 16 and 17 make point contact with the latching part 34, the edge portion 34a of the latching part 34 with which the first latched part 16 contacts moves from the position P1 to the position P3. At the same time, the edge portion 34a of the latching part 34 with which the first latched part 17 contacts moves from the position P2 to the position P4. FIGS. 10 to 12 show the transit state in which the distal end portion of the proximal end surface 16a of the first latched part 16 and the distal end portion of the proximal end surface 17a of the first latched part 17 contact the edge portion 34a of the latching part 34.

Similarly, the second arm portion 13 receives the vertical force from the edge portion 34a of the latching part 34, and moves in the opposite direction X so as to approach the first arm portion 12. At this time, the central portion 14 elastically deforms so that both ends of the central portion 14 move to the side of the center axis C1 of the holding tube 31.

In the transit state, the arm member 11 of the clip unit 10 maintains the closed state.

(Retrain Organization)

In the course of the ligation using the clip unit 10, the arm member 11 once closed can be opened again in order to change the ligating position, if necessary, and the target tissue T can be grasped again. In the present embodiment, from the initial state, if the above-described transit state is completed and before the transition to the following latched state, the target tissue T can be re-grasped.

When the operator moves the slider 102 toward the distal side with respect to the operation unit main body 101 in order to grasp the target tissue T, the compressed helical spring 39 expands. That is, when the slider 102 is moved toward the distal side with respect to the operation unit main body 101, the arm member 11 moves to the distal end side of the holding tube 31 by the action of the helical spring 39 and returns to the initial state.

The distal end of the helical spring 39 is in contact with the holding tube 31 at the proximal end of the helical spring 39 which is in contact with the arm member 11, and the arm member 11 and the operation wire 62 are connected by the hook portion 65, thereby the holding tube 31 is maintained in a state pressed against the distal end member 67 by the restoring force (biasing force) that the helical spring 39 is about to expand.

After the clip unit 10 returns to the initial state, the clip unit 10 is made to face the other target tissue T by performing the bending operation of the bending portion of the endoscope or the like. After that, by performing the aforementioned procedure, the target tissue T can be grasped again by the clip unit 10.

(Change from Transit State to Latched State)

When the slider 102 is pulled back further from the transit state, in a state where the positions of the first arm 12 and the second arm 13 in the opposing direction X and the orthogonal direction Z with respect to the holding tube 31 are maintained, the two first latched parts 16 and 17 and the second latched parts 21 and 22 pass through the inside of the latching part 34. Then, the two first latched parts 16, 17 and the second latched parts 21, 22 move beyond the latching part 34 to the proximal end side. At this time, the state in which the first arm portion 12, the second arm portion 13 and the central portion 14 are pressed against the latching part 34 is eliminated. Therefore, due to the elastic force of the central portion 14, as shown in FIGS. 10 to 12, the proximal end side of the first arm portion 12 and the proximal end side of the second arm portion 13 are moved in the opposite direction X so as to be separated from each other.

Here, when the force to move the arm member 11 toward the proximal end side of the holding tube 31 is released by using the operation wire 62, the arm member 11 receives a force that the helical spring 39 (biasing member) moves the arm member 11 to the distal end side of the holding tube 31. However, since the distal end surfaces 16b and 17b of the two first latched parts 16 and 17 are latched to the distal end side with respect to the proximal end surface 34b of the latching part 34, the arm member 11 does not move further to the distal side.

When the clip unit 10 is in the latched state, the distal end surfaces 16b and 17b of the two first latched parts 16 and 17 are latched to the proximal end surface 34b of the latching part 34, thereby the movement of the arm member 11 toward the distal side relative to the holding tube 31 is restricted. That is, the state in which the clip unit 10 grasps the target tissue T is maintained, and it becomes impossible to return to the initial state in which the first arm 12 and the second arm 13 are in the open state. Since the first arm portion 12 and the second arm portion 13 are fixed in the closed state in the clip unit 10 in the latched state, the clip unit 10 ligates the target tissue T. At this time, the central portion 14 protrudes toward the proximal end side from the holding tube 31.

(Separation of Clip Unit)

The clip unit 10 is separated from the treatment instrument main body 40 while the clip unit 10 is ligating the target tissue T.

Specifically, the procedure for separating the clip unit 10 from the treatment instrument main body 40 is as follows. When the slider 102 is pushed in, the operation wire 62 moves to the distal side with respect to the coil sheath 66. When the connecting member 63 protrudes further to the distal end side than the distal end member 67, the arm member 11 and the holding tube 31 integrally move to the distal side. Since the hook portion 65 of the connecting member 63 is located outside the holding tube 31, it can be separated from the central portion 14 of the arm member 11. For example, by operating the endoscope bending portion, it is possible to separate the hook portion 65 from the central portion 14 of the arm member 11 by mobbing the distal end of the sheath part 61. As a result, the clip unit 10 ligated with the target tissue T is indwelled in the body.

After the clip unit 10 is separated from the treatment instrument main body 40, the slider 102 is pulled back to accommodate the connecting member 63 in the sheath part 61. Further, the endoscope treatment tool 1 is pulled out from the channel of the endoscope and taken out. Then the endoscope insertion portion of the endoscope is removed from inside the body of patient. After that, necessary measures are taken and the series of procedures is completed.

As described above, in the endoscope treatment tool 1 according to the present embodiment, in the process of bringing the clip unit 10 close to the target tissue T, by performing the operation of rotating the operation wire 62 with respect to the coil sheath 66 using the operation unit main body 101, it is possible to freely rotate the arm member 11 around the central axis C1 of the holding tube 31. Therefore, according to the endoscope treatment tool 1 of the present embodiment, it is possible to easily rotate the arm member 11 so as to be in a rotational position suitable for ligation. Further, when the arm member 11 of the clip unit 10 receives an external force by bringing the clip unit 10 into contact with the target tissue T, the arm member 11 is engaged with the engagement part 33 of the holding tube 31 by this external force, thereby the rotation of the arm member 11 is restricted. Therefore, the rotational position suitable for ligation is maintained even when the clip unit 10 is brought into contact with the target tissue T.

As described above, according to the endoscope treatment tool 1 of the present embodiment, it is possible to operate the clip unit 10 in an appropriate orientation, and it is possible to prevent the orientation of the clip unit 10 from unintentionally changing upon receiving an external force.

In addition, in the endoscope treatment tool 1 of the present embodiment, the arm member 11 of the clip unit 10 can be engaged with the engagement part 33 of the holding tube 31 also by slightly pulling the operation wire 62 to the proximal side. Therefore, after operating the arm member 11 so that the arm member 11 is at the desired rotational position, the clip unit 10 can be brought close to the target tissue T while maintaining its rotational position. Therefore, according to the endoscope treatment instrument 1 of the present embodiment, even if the arm member 11 inadvertently comes into contact with another tissue or instrument before the clip unit 10 contacts the target tissue T, since the rotational position of the arm member 11 is maintained if the operation wire 62 is lightly pulled toward the operator side, there is no need to readjust the rotational position of the arm member 11.

MODIFIED EXAMPLE 1

A modified example of the above embodiment will be described.

The insertion portion 60 of the endoscope treatment tool 1A of this modified example shown in FIGS. 13 to 16 has the operation wire 70 and the connection member 74 that are different from the operation wire 62 and the connection member 63 disclosed in the above embodiment.

The operation wire 70 of this modified example has a wire main body 71, a connecting portion 72, and a loop portion 73.

The wire main body 71 has a proximal end portion similar to the operation wire 62 disclosed in the above embodiment. The distal end of the wire body part 71 of the present embodiment is fixed to the connecting portion 72.

Like the operation wire 62 disclosed in the above embodiment, the wire main body part 71 is inserted into the sheath part 61 so as to be capable of advancing and retracting. The wire main body 71 is formed of a metal single wire or a stranded wire.

The connecting portion 72 is fixed to the distal end of the wire body part 71. The connecting portion 72 connects the wire body part 71 and the loop portion 73. The connecting portion 72 is formed in a cylindrical shape with a metal or the like. The outer diameter of the connecting portion 72 is smaller than the inner diameter of the coil sheath 66. The outer diameter of the connecting portion 72 may be substantially equal to the inner diameter of the distal end member 67 or may be smaller than the inner diameter of the distal end member 67.

Further, the outer diameter of the connecting portion 72 may be larger than the inner diameter of the distal end member 67. In this case, movement of the connecting portion 72 toward the distal side from the proximal end of the distal end member 67 is limited by the distal end member 67, thereby the maximum projecting amount of the loop portion 73 and the connecting member 74 from the distal end member 67 is limited by the contact between the distal end member 67 and the connecting portion 72.

The loop portion 73 is connected to the wire body part 71 via the connecting portion 72. The loop portion 73 is formed by folding back the wire 73a. Both ends of the wire 73a are fixed to the connecting portion 72 by brazing, resistance welding, or the like.

The connecting member 74 is connected to the loop portion 73 at the distal end portion of the operation wire 62. The connecting member 74 is provided so as to be rotatable around an axis parallel to the opposite direction X with respect to the operation wire 62. The connecting member 74 includes a connecting portion main body 75, a through hole 76 formed in the proximal end portion of the connecting portion main body 75, a hook portion 77 arranged at the distal end portion of the connecting portion main body 75, and an inclined surface 78 formed in a portion opposed to the hook portion 77 in the connecting portion main body 75. The connecting member 74 is positioned in the holding tube 31 when the clip unit 10 is in the initial state.

By inserting the folded back portion of the wire 73a of the loop portion 73 through the through hole 76, the connecting member 74 is rotatable around the axis parallel to the opposing direction X with respect to the loop portion 73 (rotatable in the direction of the arrow D in FIG. 2). The width of the connecting member 74 (the outer diameter of the connecting portion main body 75 in the direction perpendicular to the central axis C1 of the holding tube 31 when the hook portion 77 is disposed on the distal end side) is slightly smaller than the inner diameter of the helical spring 39, the inner diameter of the coil sheath 66, and the inner diameter of the distal end member 67. That is, the connecting member 74 cannot rotate with respect to the loop portion 73 from the state in which the hook portion 77 is disposed at the distal end side in the holding tube 31 and the sheath part 61. In other words, relative movement in the radial direction between the arm member 11 and the hook portion 77 is restricted by the holding tube 31 and the sheath part 61.

As used herein, the description "the connecting member 74 cannot rotate with respect to the loop portion 73" means that the connecting member 74 cannot rotate with respect to the loop portion 73 until the engagement between the hook portion 77 and the central portion 14 is released. Therefore, the description "the connecting member 74 cannot rotate with respect to the loop portion 73" does not mean literally that the connecting member 74 cannot rotate with respect to the loop portion 73 even at a slight angle. By disposing the central portion 14 between the hook portion 77 and the inclined surface 78 of the connecting member 74, the hook portion 77 can engage with the central portion 14. When the hook portion 77 is rotated in the direction D (see FIG. 2) relative to the loop portion 73, the engagement between the hook portion 77 and the central portion 14 is released. In this way, the connecting member 74 is detachably connected to the arm member 11.

In this modified example, the behavior of the connecting member 74 when separating the clip unit 10 from the treatment instrument main body 40 is different from the above embodiment.

Figure 15:
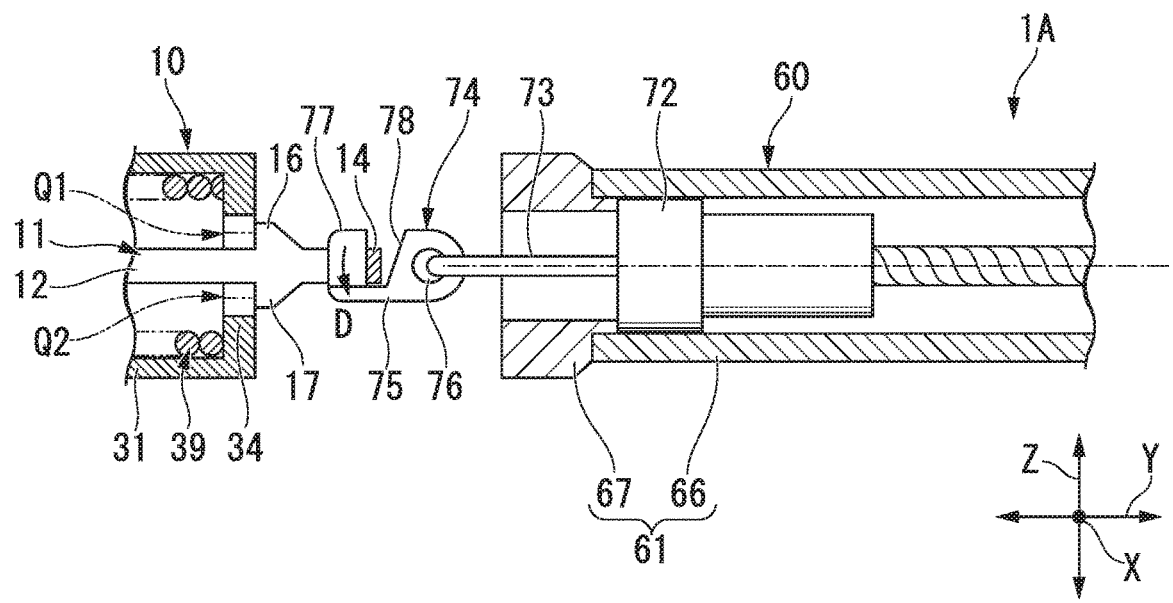
FIG. 15 is a diagram for explaining the operation of the endoscope treatment tool.
Figure 16:
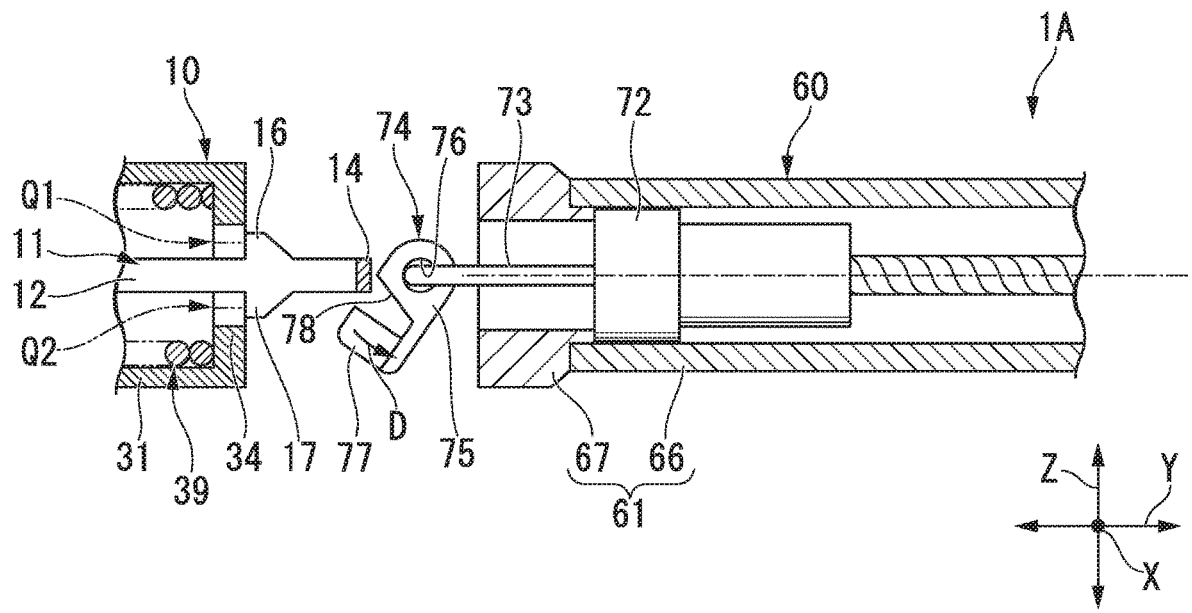
FIG. 16 is a view for explaining the operation of the endoscope treatment tool.

Specifically, the procedure for separating the clip unit 10 from the treatment instrument main body 40 is as follows. When the slider 102 is pushed in, the operation wire 62 moves to the distal side with respect to the coil sheath 66. When the connecting member 74 protrudes toward the distal end side from the distal end member 67, the arm member 11 and the holding tube 31 integrally move to the distal side. Since the connecting member 74 is positioned outside the holding tube 31, the connecting member 74 can be rotated with respect to the loop portion 73. When the slider 102 is pushed and the operation wire 62 is moved to the distal end side, the inclined surface 78 of the connecting member 74 comes into contact with the proximal end surface of the central portion 14 of the clip unit 10 which ligates the target tissue T. As shown in FIGS. 15 and 16, the hook portion 77 is rotated in the direction D together with the connecting portion main body 75 while being guided by the inclined surface 78, and the engagement between the hook portion 77 and the central portion 14 is released. As a result, the clip unit 10 ligated with the target tissue T is indwelled in the body.

MODIFIED EXAMPLE 2

Another modified example of the above embodiment will be described.

Figure 17:
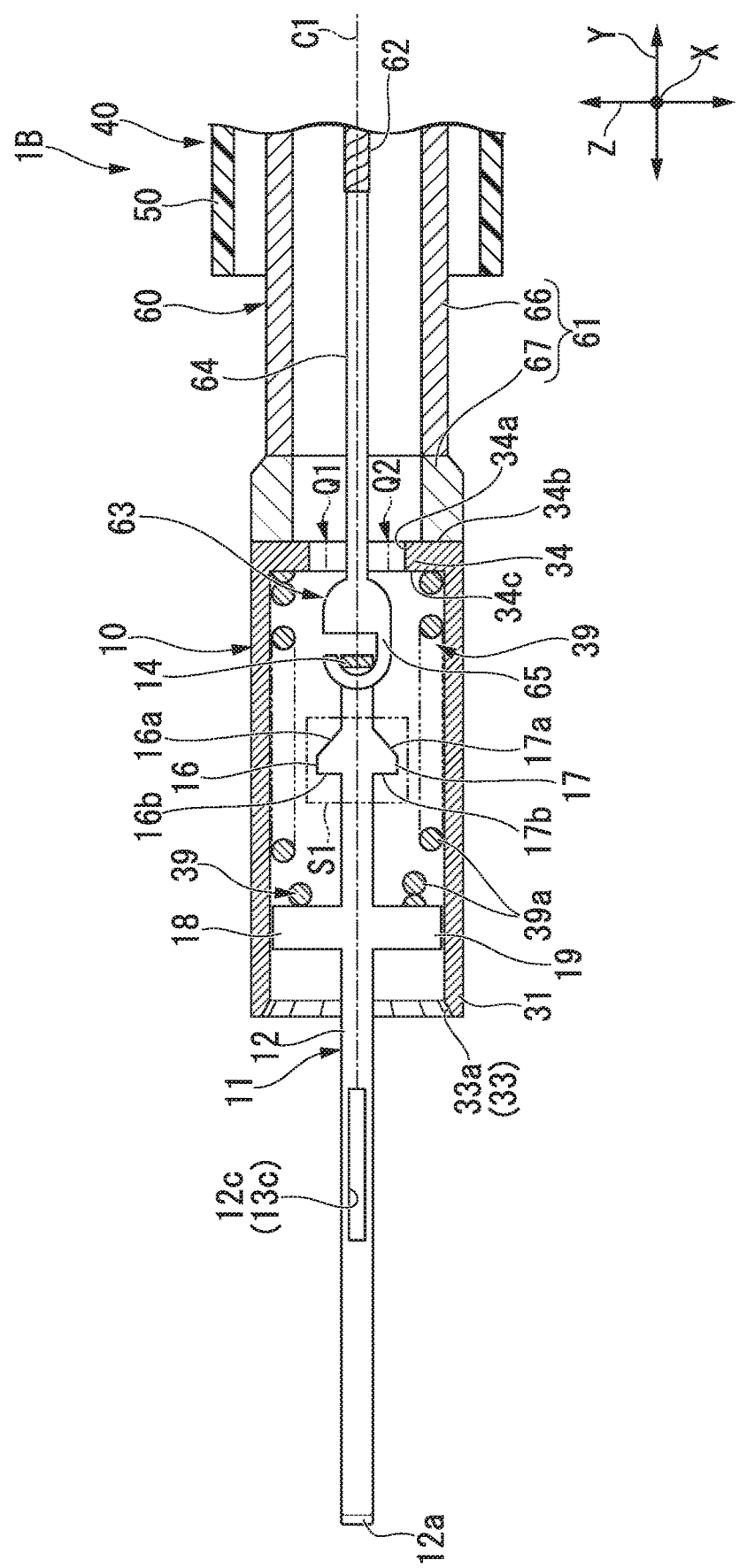
FIG. 17 is a partial cross-sectional view showing still another modified example of the endoscope treatment tool.

In the endoscope treatment tool 1B of this modified example shown in FIG. 17, in place of the projections 12b and 13b formed on the first arm portion 12 and the second arm portion 13 of the arm member 11, through holes 12c and 13c are formed at the positions similar to the projections 12b and 13b. The through holes 12c and 13c constitute a rotation restricting structure for preventing the arm member 11 from rotating around the center axis C1 of the holding tube 31.

In this modified example, the convex portion of the concave-convex portion 33a of the engagement part 33 enters the through holes 12c and 13c of the arm member 11, whereby the rotational motion of the arm member 11 around the central axis C1 of the holding tube 31 can be restricted.

Even if the concave portion formed by recess that does not penetrating the first arm portion 12 and the second arm portion 13 is formed in the first arm portion 12 and the second arm portion 13 in place of the through holes 12c and 13c, it functions as a rotation restricting structure similarly to the through holes 12c and 13c of this modified example.

MODIFIED EXAMPLES 3

Another modified example of the above embodiment will be described.

Figure 18:
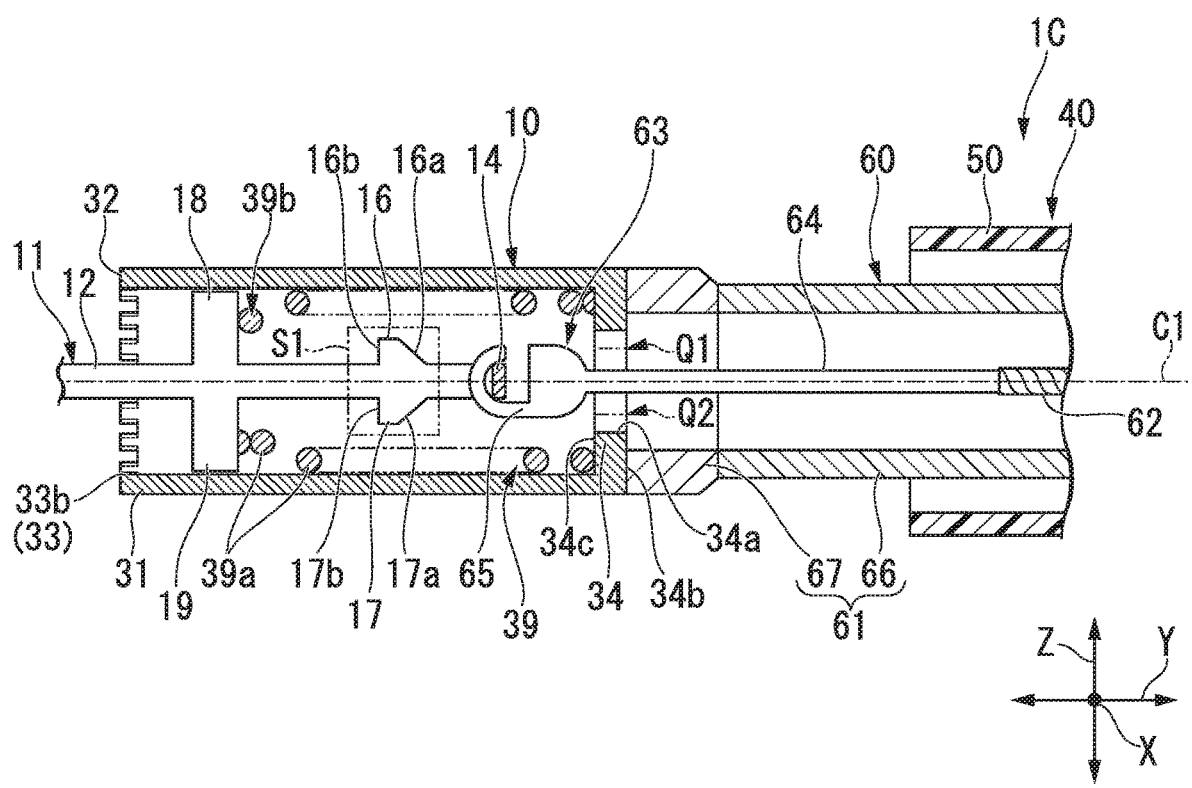
FIG. 18 is a partial cross-sectional view showing still another modified example of the endoscope treatment tool.

In the endoscope treatment tool 1C of this modified example shown in FIG. 18, a concave-convex portion 33b is formed on the distal end surface 32 of the holding tube 31. That is, in this modified example, the engagement part 33 is arranged on the distal end surface 32 of the holding tube 31.

The concave portion of the concavo-convex portion 33b formed on the distal end surface 32 of the holding tube 31 is a recess having a size that the projections 12b and 13b formed on the first arm portion 12 and the second arm portion 13 of the arm member 11 can enter.

With such a configuration as well, it is possible to restrict the rotational motion of the arm member 11 about the central axis C1 of the holding tube 31.

MODIFIED EXAMPLE 4

Another modified example of the above embodiment will be described.

In the endoscope treatment tool of this modified example, the holding tube 31 having the concave-convex portion 33b disclosed in the above-described modified example 3 is combined with the first arm portion 12 and the second arm portion 13 having the through holes 12c and 13c disclosed in the above-described modified example 2.

In this modified example, the convex portion of the concavo-convex portion 33b formed on the distal end surface 32 of the holding tube 31 can enter the through holes 12c and 13c formed in the first arm portion 12 and the second arm portion 13 of the arm member 11.

With such a configuration as well, it is possible to restrict the rotational motion of the arm member 11 about the central axis C1 of the holding tube 31.

While the embodiments of the present invention have been described above, the technical scope of the present invention is not limited to the above-described embodiments, and various combinations of constituent elements in each embodiment may be changed without departing from the spirit of the present invention. It is possible to make various changes to each component or delete it. The invention is not limited by the foregoing description, but only by the scope of the appended claims.

What is claimed is:

1. An endoscope treatment tool comprising:
a tubular sheath part;
an operation wire arranged inside the sheath part and capable of protruding from and retracting into a distal end of the sheath part;
an arm member connected to a distal end of the operation wire, having a pair of distal end portions, and capable of opening and closing, the arm member being rotatable integrally with the operation wire;
a holding tube arranged at the distal end of the sheath part, a portion of the arm member being inserted in the holding tube; and
a biasing member having a biasing force for moving the arm member toward a distal end side of the holding tube,
wherein the sheath part includes
an elongated body part, and
a tubular member fixed to a distal end of the body part,
in a state where the holding tube and the tubular member are in contact with each other, the holding tube and the tubular member are connected to each other so as not to be rotated relative to each other about an axis and to be movable relative to each other in a direction in which a central axis of the sheath part extends,
the arm member and the holding tube have a rotation restricting structure that prevents the arm member from rotating about an axis of the holding tube in a state where the arm member is in contact with the holding tube and held against the biasing force of the biasing member, and
the arm member rotates integrally with the operation wire in a state where the arm member is moved distally relative to the holding tube by the biasing force of the biasing member, in order to disengage the rotation restricting structure.

2. The endoscope treatment tool according to claim 1, wherein the rotation restricting structure includes:
an engagement part provided in the holding tube and engages with the arm member when the arm member comes into contact with the holding tube against the biasing force of the biasing member; and
an engaged part provided on the arm member and engaged with the engagement part.

3. The endoscope treatment tool according to claim 2, wherein
the engagement part is a concave portion provided on the holding tube, and
the engaged part is a projection protruding from the arm member and capable of entering the concave portion.

4. The endoscope treatment tool according to claim 2, wherein
the engagement part is a convex portion provided on the holding tube, and
the engaged part is a recess formed in the arm member and into which the convex portion can enter.

5. The endoscope treatment tool according to claim 1, wherein
the biasing member is composed of a spring disposed inside the holding tube, and
the arm member is separated from a distal end of the holding tube by the biasing force of the spring in a state where an operation force is not applied to the operation wire.

6. The endoscope treatment tool according to claim 1, further comprising an operation unit connected to a proximal end of the sheath part and moving the operation wire forward and backward.

7. The endoscope treatment tool according to claim 1, further comprising a connecting member that connects between the operation wire and the arm member,
wherein the connecting member is configured to release a connection between the operation wire and the arm member when the arm member is closed.

* * * * *